United States Patent
Huber et al.

(10) Patent No.: US 9,651,539 B2
(45) Date of Patent: May 16, 2017

(54) REDUCING BACKGROUND FLUORESCENCE IN MEMS MATERIALS BY LOW ENERGY ION BEAM TREATMENT

(71) Applicant: Quantapore, Inc., Menlo Park, CA (US)

(72) Inventors: Martin Huber, Menlo Park, CA (US); Bason E. Clancy, Redwood City, CA (US); Adam R. Hall, Clemmons, NC (US)

(73) Assignee: Quantapore, Inc., Menlo Park, CA (US)

( * ) Notice: Subject to any disclaimer, the term of this patent is extended or adjusted under 35 U.S.C. 154(b) by 0 days.

(21) Appl. No.: 14/659,432

(22) Filed: Mar. 16, 2015

(65) Prior Publication Data

US 2016/0077078 A1    Mar. 17, 2016

Related U.S. Application Data

(63) Continuation of application No. PCT/US2013/067126, filed on Oct. 28, 2013, which
(Continued)

(51) Int. Cl.
*G01N 33/487* (2006.01)
*B81C 1/00* (2006.01)
(Continued)

(52) U.S. Cl.
CPC ......... *G01N 33/48721* (2013.01); *B81B 7/02* (2013.01); *B81C 1/00206* (2013.01);
(Continued)

(58) Field of Classification Search
CPC ........... G01N 33/487; G01N 33/48707; G01N 33/48721; B81B 7/02; B81B 1/00206;
(Continued)

(56) References Cited

U.S. PATENT DOCUMENTS 4,161,690 A    7/1979 Feier
4,962,037 A    10/1990 Jett et al.
(Continued)

FOREIGN PATENT DOCUMENTS

CN    1403817    3/2003
CN    201302544    9/2009
(Continued)

OTHER PUBLICATIONS

US 8,008,014, 08/2011, Gershow et al. (withdrawn)
(Continued)

*Primary Examiner* — David E Smith
(74) *Attorney, Agent, or Firm* — Levine Bagade Han LLp

(57) ABSTRACT

Methods for fabricating materials useful for optical detection in microfluidic and nanofluidic devices, such as those used in nanopore-based nucleic acid sequencing are described herein. In certain variations, a method of reducing background fluorescence in a MEMS material may include the step of treating a surface of the MEMS material with a low energy ion beam.

6 Claims, 8 Drawing Sheets

Related U.S. Application Data is a continuation-in-part of application No. 13/662,532, filed on Oct. 28, 2012.

(60) Provisional application No. 61/819,606, filed on May 5, 2013.

(51) Int. Cl.
  *B81B 7/02* (2006.01)
  *C12Q 1/68* (2006.01)

(52) U.S. Cl.
  CPC .......... *C12Q 1/6818* (2013.01); *C12Q 1/6869* (2013.01); *B81B 2201/0214* (2013.01); *B81B 2201/047* (2013.01); *B81B 2203/0353* (2013.01)

(58) Field of Classification Search
  CPC ...... B81B 2201/047; B81B 2201/0214; B81B 2201/0353; C12Q 1/6818; C12Q 1/6876; H01J 37/30; H01J 37/317; H01J 37/32
  See application file for complete search history.

(56) References Cited

U.S. PATENT DOCUMENTS

| | | |
|---|---|---|
| 5,131,755 A | 7/1992 | Chadwick et al. |
| 5,356,776 A | 10/1994 | Kambara et al. |
| 5,387,926 A | 2/1995 | Bellan |
| 5,405,747 A | 4/1995 | Jett et al. |
| 5,470,705 A | 11/1995 | Grossman et al. |
| 5,580,732 A | 12/1996 | Grossman et al. |
| 5,624,800 A | 4/1997 | Grossman et al. |
| 5,795,782 A | 8/1998 | Church et al. |
| 5,798,042 A | 8/1998 | Chu et al. |
| 5,821,058 A | 10/1998 | Smith et al. |
| 5,858,559 A * | 1/1999 | Barbour ............... H01L 33/346 428/620 |
| 5,945,312 A | 8/1999 | Goodman et al. |
| 5,989,871 A | 11/1999 | Grossman et al. |
| 6,015,714 A | 1/2000 | Baldarelli et al. |
| 6,136,543 A | 10/2000 | Anazawa et al. |
| 6,210,896 B1 | 4/2001 | Chan |
| 6,211,955 B1 | 4/2001 | Basiji et al. |
| 6,249,341 B1 | 6/2001 | Basiji et al. |
| 6,251,303 B1 | 6/2001 | Bawendi et al. |
| 6,252,303 B1 | 6/2001 | Huang |
| 6,263,286 B1 | 7/2001 | Gilmanshin et al. |
| 6,267,872 B1 | 7/2001 | Akeson et al. |
| 6,325,968 B1 | 12/2001 | Fricker et al. |
| 6,335,420 B1 | 1/2002 | Bruening et al. |
| 6,335,440 B1 | 1/2002 | Lee et al. |
| 6,355,420 B1 | 3/2002 | Chan |
| 6,362,002 B1 | 3/2002 | Denison et al. |
| 6,413,792 B1 | 7/2002 | Sauer et al. |
| 6,426,231 B1 | 7/2002 | Bayley et al. |
| 6,428,959 B1 | 8/2002 | Deamer |
| 6,429,897 B2 | 8/2002 | Derndinger et al. |
| 6,447,724 B1 | 9/2002 | Jensen et al. |
| 6,464,842 B1 | 10/2002 | Golovchenko et al. |
| 6,465,193 B2 | 10/2002 | Akeson et al. |
| 6,473,176 B2 | 10/2002 | Basiji et al. |
| 6,498,010 B1 | 12/2002 | Fitzgerald et al. |
| 6,503,757 B1 | 1/2003 | Chow |
| 6,504,943 B1 | 1/2003 | Sweatt et al. |
| 6,511,802 B1 | 1/2003 | Albrecht et al. |
| 6,528,258 B1 | 3/2003 | Russell |
| 6,537,755 B1 | 3/2003 | Drmanac |
| 6,583,865 B2 | 6/2003 | Basiji et al. |
| 6,608,680 B2 | 8/2003 | Basiji et al. |
| 6,608,682 B2 | 8/2003 | Ortyn et al. |
| 6,616,895 B2 | 9/2003 | Dugas et al. |
| 6,617,113 B2 | 9/2003 | Deamer |
| 6,618,140 B2 | 9/2003 | Frost et al. |
| 6,618,679 B2 | 9/2003 | Loehrlein et al. |
| 6,627,067 B1 | 9/2003 | Branton et al. |
| 6,671,044 B2 | 12/2003 | Ortyn et al. |
| 6,673,615 B2 | 1/2004 | Denison et al. |
| 6,706,203 B2 | 3/2004 | Barth et al. |
| 6,723,515 B2 | 4/2004 | Barron |
| 6,743,905 B2 | 6/2004 | Woo et al. |
| 6,746,594 B2 | 6/2004 | Akeson et al. |
| 6,752,914 B1 | 6/2004 | Hassard |
| 6,756,204 B2 | 6/2004 | Grossman et al. |
| 6,758,961 B1 | 7/2004 | Vogel et al. |
| 6,772,070 B2 | 8/2004 | Gilmanshin et al. |
| 6,790,671 B1 | 9/2004 | Austin et al. |
| 6,821,726 B1 | 11/2004 | Dahm et al. |
| 6,824,659 B2 | 11/2004 | Bayley et al. |
| 6,830,670 B1 | 12/2004 | Viovy et al. |
| 6,855,551 B2 | 2/2005 | Bawendi et al. |
| 6,856,390 B2 | 2/2005 | Nordman et al. |
| 6,906,749 B1 | 6/2005 | Fox |
| 6,916,665 B2 | 7/2005 | Bayley et al. |
| 6,936,433 B2 | 8/2005 | Akeson et al. |
| 6,947,128 B2 | 9/2005 | Basiji et al. |
| 6,952,651 B2 | 10/2005 | Su |
| 6,975,400 B2 | 12/2005 | Ortyn et al. |
| 6,982,146 B1 | 1/2006 | Schneider et al. |
| 6,998,251 B2 | 2/2006 | Guttman et al. |
| 7,001,792 B2 | 2/2006 | Sauer et al. |
| 7,005,264 B2 | 2/2006 | Su et al. |
| 7,008,547 B2 | 3/2006 | Chen et al. |
| 7,049,104 B2 | 5/2006 | Kambara et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,060,507 B2 | 6/2006 | Akeson et al. |
| 7,074,569 B2 | 7/2006 | Woo et al. |
| 7,129,050 B2 | 10/2006 | Grossman et al. |
| 7,189,503 B2 | 3/2007 | Akeson et al. |
| 7,201,836 B2 | 4/2007 | Vogel et al. |
| 7,235,184 B2 | 6/2007 | Dugas et al. |
| 7,235,361 B2 | 6/2007 | Bawendi et al. |
| 7,238,485 B2 | 7/2007 | Akeson et al. |
| 7,244,349 B2 | 7/2007 | Vogel et al. |
| 7,248,771 B2 | 7/2007 | Schmidt et al. |
| 7,250,115 B2 | 7/2007 | Barth |
| 7,271,896 B2 | 9/2007 | Chan et al. |
| 7,279,337 B2 | 10/2007 | Zhu |
| 7,280,207 B2 | 10/2007 | Oldham et al. |
| 7,285,010 B2 | 10/2007 | Hatakeyama et al. |
| 7,364,851 B2 | 4/2008 | Berlin et al. |
| 7,371,533 B2 | 5/2008 | Slater et al. |
| 7,381,315 B2 | 6/2008 | Grossman et al. |
| 7,387,715 B2 | 6/2008 | Vogel et al. |
| 7,390,457 B2 | 6/2008 | Schembri |
| 7,397,232 B2 | 7/2008 | Hu et al. |
| 7,410,564 B2 | 8/2008 | Flory |
| 7,428,047 B2 | 9/2008 | Oldham et al. |
| 7,438,193 B2 | 10/2008 | Yang et al. |
| 7,444,053 B2 | 10/2008 | Schmidt et al. |
| 7,468,271 B2 | 12/2008 | Golovchenko et al. |
| 7,476,503 B2 | 1/2009 | Turner et al. |
| 7,553,730 B2 | 6/2009 | Barth et al. |
| 7,567,695 B2 | 7/2009 | Frost et al. |
| 7,595,023 B2 | 9/2009 | Lewis et al. |
| 7,609,309 B2 | 10/2009 | Brown et al. |
| 7,622,934 B2 | 11/2009 | Hibbs et al. |
| 7,625,706 B2 | 12/2009 | Akeson et al. |
| 7,651,599 B2 | 1/2010 | Blaga et al. |
| 7,666,593 B2 | 2/2010 | Lapidus |
| 7,670,770 B2 | 3/2010 | Chou et al. |
| 7,678,562 B2 | 3/2010 | Ling |
| 7,744,816 B2 | 6/2010 | Su et al. |
| 7,777,505 B2 | 8/2010 | White et al. |
| 7,803,607 B2 | 9/2010 | Branton et al. |
| 7,835,870 B2 | 11/2010 | Nair et al. |
| 7,838,873 B2 | 11/2010 | Clevenger et al. |
| 7,843,562 B2 | 11/2010 | Chan et al. |
| 7,846,738 B2 | 12/2010 | Golovchenko et al. |
| 7,849,581 B2 | 12/2010 | White et al. |
| 7,871,777 B2 | 1/2011 | Schneider et al. |
| 7,883,869 B2 | 2/2011 | Ju et al. |

(56) References Cited

U.S. PATENT DOCUMENTS

| | | |
|---|---|---|
| 7,897,338 B2 | 3/2011 | Woo et al. |
| 7,947,454 B2 | 5/2011 | Akeson et al. |
| 7,972,858 B2 | 7/2011 | Meller et al. |
| 8,105,846 B2 | 1/2012 | Bayley et al. |
| 8,206,568 B2 | 6/2012 | Branton et al. |
| 8,394,584 B2 | 3/2013 | Timp et al. |
| 8,394,640 B2 | 3/2013 | Golovchenko et al. |
| 8,435,775 B2 | 5/2013 | Holliger et al. |
| 8,440,403 B2 | 5/2013 | Frayling |
| 8,771,491 B2 | 7/2014 | Huber |
| 8,802,838 B2 | 8/2014 | Meller et al. |
| 8,865,078 B2 | 10/2014 | Chiou et al. |
| 8,865,455 B2 | 10/2014 | Frayling |
| 9,121,843 B2 | 9/2015 | Meller et al. |
| 2002/0034762 A1 | 3/2002 | Muller et al. |
| 2002/0119455 A1 | 8/2002 | Chan |
| 2003/0003463 A1 | 1/2003 | Rothberg et al. |
| 2003/0064366 A1 | 4/2003 | Hardin et al. |
| 2003/0092005 A1 | 5/2003 | Levene et al. |
| 2003/0096220 A1 | 5/2003 | Lafferty et al. |
| 2003/0143614 A1 | 7/2003 | Drmanac |
| 2003/0148544 A1 | 8/2003 | Nie et al. |
| 2003/0174992 A1 | 9/2003 | Levene et al. |
| 2003/0207326 A1 | 11/2003 | Su et al. |
| 2003/0215881 A1 | 11/2003 | Bayley et al. |
| 2004/0002089 A1 | 1/2004 | Dubertret et al. |
| 2004/0033492 A1 | 2/2004 | Chen |
| 2004/0137158 A1* | 7/2004 | Kools ............... C23C 14/5826 427/404 |
| 2004/0146430 A1 | 7/2004 | Dugas |
| 2004/0175710 A1 | 9/2004 | Haushalter |
| 2004/0214221 A1 | 10/2004 | Muehlegger et al. |
| 2005/0014154 A1 | 1/2005 | Weizenegger |
| 2005/0019784 A1 | 1/2005 | Su et al. |
| 2005/0095599 A1 | 5/2005 | Pittaro et al. |
| 2005/0130159 A1 | 6/2005 | Rigler et al. |
| 2005/0130173 A1 | 6/2005 | Leamon et al. |
| 2005/0136408 A1 | 6/2005 | Tom et al. |
| 2005/0147992 A1 | 7/2005 | Quake et al. |
| 2005/0153284 A1 | 7/2005 | Foldes et al. |
| 2005/0164211 A1 | 7/2005 | Hannah |
| 2005/0186576 A1 | 8/2005 | Chan et al. |
| 2005/0186629 A1 | 8/2005 | Barth |
| 2005/0196876 A1 | 9/2005 | Chan et al. |
| 2005/0227239 A1 | 10/2005 | Joyce |
| 2005/0241933 A1 | 11/2005 | Branton et al. |
| 2005/0282229 A1 | 12/2005 | Su et al. |
| 2006/0003458 A1 | 1/2006 | Golovchenko et al. |
| 2006/0019247 A1 | 1/2006 | Su et al. |
| 2006/0019259 A1 | 1/2006 | Joyce |
| 2006/0063171 A1 | 3/2006 | Akeson et al. |
| 2006/0147942 A1 | 7/2006 | Buzby |
| 2006/0210995 A1 | 9/2006 | Joyce |
| 2006/0214105 A1* | 9/2006 | Jaccard ............... B81C 1/00492 250/307 |
| 2006/0231419 A1 | 10/2006 | Barth et al. |
| 2006/0251371 A1 | 11/2006 | Schmidt et al. |
| 2006/0292041 A1 | 12/2006 | Dugas et al. |
| 2007/0012865 A1 | 1/2007 | Katzir et al. |
| 2007/0037199 A1 | 2/2007 | Takahashi et al. |
| 2007/0042366 A1 | 2/2007 | Ling |
| 2007/0054276 A1 | 3/2007 | Sampson |
| 2007/0172858 A1 | 7/2007 | Hardin et al. |
| 2007/0172865 A1 | 7/2007 | Hardin et al. |
| 2007/0190542 A1 | 8/2007 | Ling et al. |
| 2007/0190543 A1 | 8/2007 | Livak |
| 2007/0202008 A1 | 8/2007 | Schembri et al. |
| 2007/0215472 A1 | 9/2007 | Slater et al. |
| 2007/0218494 A1 | 9/2007 | Slater et al. |
| 2007/0224613 A1 | 9/2007 | Strathmann |
| 2007/0231795 A1 | 10/2007 | Su |
| 2007/0264623 A1 | 11/2007 | Wang et al. |
| 2008/0025875 A1 | 1/2008 | Martin et al. |
| 2008/0032290 A1 | 2/2008 | Young |
| 2008/0050752 A1 | 2/2008 | Sun et al. |
| 2008/0187915 A1 | 8/2008 | Polonsky et al. |
| 2008/0193956 A1 | 8/2008 | Kricka et al. |
| 2008/0254995 A1 | 10/2008 | Kim et al. |
| 2008/0261204 A1 | 10/2008 | Lexow |
| 2008/0274905 A1 | 11/2008 | Greene |
| 2008/0311375 A1 | 12/2008 | Harnack et al. |
| 2009/0021735 A1 | 1/2009 | Oldham et al. |
| 2009/0024331 A1 | 1/2009 | Tomaney et al. |
| 2009/0029477 A1 | 1/2009 | Meller et al. |
| 2009/0035777 A1 | 2/2009 | Kokoris et al. |
| 2009/0061447 A1 | 3/2009 | Schneider |
| 2009/0066315 A1 | 3/2009 | Hu et al. |
| 2009/0136958 A1 | 5/2009 | Gershow et al. |
| 2009/0137007 A1 | 5/2009 | Korlach et al. |
| 2009/0140170 A1* | 6/2009 | Nevil ............... B01L 3/502707 250/484.4 |
| 2009/0148348 A1 | 6/2009 | Pettigrew et al. |
| 2009/0185955 A1 | 7/2009 | Nellissen |
| 2009/0222216 A1 | 9/2009 | Hibbs et al. |
| 2009/0250615 A1 | 10/2009 | Oldham et al. |
| 2009/0277869 A1 | 11/2009 | Dugas |
| 2009/0298075 A1 | 12/2009 | Travers et al. |
| 2009/0305278 A1 | 12/2009 | Hardin et al. |
| 2009/0314939 A1 | 12/2009 | Stern et al. |
| 2010/0025249 A1 | 2/2010 | Polonsky et al. |
| 2010/0029508 A1 | 2/2010 | Austin et al. |
| 2010/0035260 A1 | 2/2010 | Olasagasti et al. |
| 2010/0035268 A1 | 2/2010 | Beechem et al. |
| 2010/0075309 A1 | 3/2010 | Maxham et al. |
| 2010/0103416 A1 | 4/2010 | Oldham et al. |
| 2010/0227913 A1 | 9/2010 | Lyakhov et al. |
| 2010/0262379 A1 | 10/2010 | Frazier |
| 2010/0292101 A1 | 11/2010 | So |
| 2010/0331194 A1 | 12/2010 | Turner et al. |
| 2011/0053284 A1 | 3/2011 | Meller et al. |
| 2011/0172404 A1 | 7/2011 | Luo et al. |
| 2011/0177498 A1 | 7/2011 | Clarke et al. |
| 2011/0177978 A1 | 7/2011 | Luo et al. |
| 2011/0257043 A1 | 10/2011 | Meller et al. |
| 2011/0296903 A1* | 12/2011 | Cao ............... B01L 3/502761 73/64.56 |
| 2011/0308950 A1 | 12/2011 | Sakai et al. |
| 2012/0055792 A1 | 3/2012 | Gundlach et al. |
| 2012/0135410 A1 | 5/2012 | Soni et al. |
| 2012/0199482 A1 | 8/2012 | Meller et al. |
| 2012/0261261 A1 | 10/2012 | Huber |
| 2013/0040827 A1 | 2/2013 | Macevicz |
| 2013/0176563 A1 | 7/2013 | Ozawa et al. |
| 2013/0203050 A1 | 8/2013 | Huber et al. |
| 2013/0203610 A1 | 8/2013 | Meller et al. |
| 2013/0256118 A1 | 10/2013 | Meller et al. |
| 2014/0087474 A1 | 3/2014 | Huber |
| 2014/0255935 A1 | 9/2014 | Huber |
| 2014/0367259 A1 | 12/2014 | Frayling et al. |
| 2015/0204840 A1 | 7/2015 | Soares et al. |

FOREIGN PATENT DOCUMENTS

| | | |
|---|---|---|
| EP | 1682673 | 7/2006 |
| WO | WO 2001/18247 | 3/2001 |
| WO | WO 2005/045392 | 5/2005 |
| WO | WO 2006/052882 | 5/2006 |
| WO | WO 2008/049795 | 5/2008 |
| WO | WO 2008/092760 | 8/2008 |
| WO | WO 2009/007743 | 1/2009 |
| WO | WO 2009/020682 | 2/2009 |
| WO | WO 2009/056831 | 5/2009 |
| WO | WO 2009/092035 | 7/2009 |
| WO | WO 2010/002883 | 1/2010 |
| WO | WO 2010/007537 | 1/2010 |
| WO | WO 2010/116595 | 10/2010 |
| WO | WO 2011/040996 | 4/2011 |
| WO | WO 2011/050147 | 4/2011 |
| WO | WO 2011/067559 | 4/2011 |
| WO | WO 2012/121756 | 9/2012 |
| WO | WO 2012/170499 | 12/2012 |
| WO | WO 2014/066902 | 5/2014 |

(56) References Cited

FOREIGN PATENT DOCUMENTS

| | | |
|---|---|---|
| WO | WO 2014/066905 | 5/2014 |
| WO | WO 2014/190322 | 11/2014 |

OTHER PUBLICATIONS

Cherf, G. et al, "Automated forward and reverse ratcheting of DNA in a nanopore at 5-A precision," *Nat Biotechnol.*, 30(4), 6 pages, Feb. 14, 2012.

Clarke, J. et al, "Continuous base identification for single-molecule nanopore DNA sequencing," *Nature Nanotechnology*, 4(4), pp. 265-270, Apr. 2009.

Deblois, R. et al, "Counting and Sizing of Submicron Particles by the Resistive Pulse Technique," *Rev. Sci. Instruments*, 41(7), pp. 909-916, Jul. 1970.

Dekker, C. "Solid-state nanopores," *Nature Nanotechnology*, vol. 2, pp. 209-215, Apr. 2007.

Galla et al. "Microfluidic carbon-blackened polydimethylsiloxane device with reduced ultra violet 1-4 background fluorescence for simultaneous two-color ultra violetlvisible-laser induced fluorescence detection in single cell analysis," *Biomicrofluidics* 6, pp. 014104-1 to 014104-10, Jan. 12, 2012.

Grayson, A. et al, "A BioMEMS Review: MEMS Technology for Physiologically Integrated Devices," *Proceedings IEEE*, 92(1), pp. 6-21, Jan. 2004.

Ha, T. et al., "Probing the interaction between two single molecules: fluorescence resonance energy transfer between a single donor and a single acceptor," *Proc. Natl. Acad. Sci USA*, vol. 93, No. 13, pp. 6264-6268, Jun. 25, 1996.

Heins, E.A. et al., "Detecting Single Porphyrin Molecules in a Conically Shaped Synthetic Nanopore," *Nano Letters*, 5(9), pp. 1824-1829, Jul. 26, 2005.

Henriquez, R. et al, "The resurgence of Coulter counting for analyzing nanoscale objects," *The Analyst*, 129, pp. 478-482, 2004.

Hoevel, T. et al., "Cisplatin-Digoxigenin mRNA labeling for non-radioactive detection of mRNA hybridized onto nucleic acid cDNA arrays," *Biotechniques*, vol. 27, No. 5, pp. 1064-1067, Nov. 1999.

Hsieh et al. "Effective Enhancement of Fluorescence Detection Efficiency in Protein MlcroarrayAssays: Application of a Highly Auorlnated Organosllane as the Blocking Agent on the Background Surface by a Facile Vapor-Phase Deposition Process," *Anal. Chem.*, 88:7908-7916, 2009.

Iqbal, S. M. et al., "Solid-state nanopore channels with DNA selectivity," *Nature Nanotechnology*, pp. 1-6, Apr. 1, 2007.

Ito, T. et al., "Observation of DNA transport through a single carbon nanotube channel using fluorescence microscopy," *Chem. Commun*, vol. 12, pp. 1482-1483, 2003.

Jagtiani, A. et al, "A label-free high throughput resistive-pulse sensor for simultaneous differentiation and measurement of multiple particle-laden analytes," *J. Micromech. Microeng.*, 16, pp. 1530-1539, 2006.

Kasianowicz, J.J. et al., "Characterization of Individual Polynucleotide Molecules Using a Membrane Channel," *Proc. Natl. Acad. Sci USA*, vol. 93, pp. 13770-13773, Nov. 1996.

Lee et al. "High aspect ratio polymer microstructures and cantilevers for bIoMEMS using low energy ion beam and photolithography," *Sensors and Actuators A*, 71:144-149, Apr. 1998.

Li, J. et al., "Nanoscale Ion Beam Sculpting," *Nature*, vol. 412, 11 pages, Jul. 12, 2001.

Lo, C.J. et al., "Fabrication of symmetric sub-5 nm nanopores using focused ion and electron beams," *Nanotechnology*, vol. 17, No. 13, pp. 3264-3267, Jul. 2006.

Lu et al. "Parylene Background Fluorescence Study for Biomems Applications," *Transducers*, pp. 176-179, Jun. 21-25, 2009.

Manrao, E. et al. "Reading DNA at single-nucleotide resolution with a mutant MspA nanopore and phi29 DNA polymerase," *Nat Biotechnol*, 30(4), 6 pages, Mar. 25, 2012.

McNally, et al. "Optical recognition of converted DNA nucleotides for single-molecule DNA sequencing using nanopore arrays," *Nano Letters*, vol. 10, No. 6; pp. 2237-2244, Jun. 9, 2010.

Nakane, J. et al, "Evaluation of nanopores as candidates for electronic analyte dectection," *Electrophoresis*, vol. 23, pp. 2592-2601, 2002.

Nakane, J. et al, "Nanopore sensors for nucleic acid analysis," *J. Phys. Condens. Matter*, Matter 15, pp. R1365-R1393, 2003.

Rasnik, I. et al., "Nonblinking and long-lasting single-molecule fluorescence imaging," *Nature Methods*, 3(11), pp. 891-893, Nov. 2006.

Rhee, M. et al., "Nanopore Sequencing Technology: Nanopore Preparations," *Trends in Biotechnology*, vol. 25, No. 4, pp. 174-181, Apr. 2007.

Schumacher, S. et al, "Highly-integrated lab-on-chip system for point-of-care multiparameter analysis," *Lab on a Chip*, 12(3), pp. 464-473, 2012.

Song, L. et al., "Structure of Staphylococcal alpha-hemolysin, a heptameric transmembrane protein," *Science*, vol. 274, No. 5294, pp. 1859-1866, Dec. 13, 1996.

Storm, A. J. et al. "Fabrication of solid-state nanopores with single-nanometre precision," *Nature Materials*, vol. 2, pp. 537-540, Aug. 2003.

Stryer, L., "Fluorescence Energy Transfer as a Spectroscopic Ruler," *Annual Review of Biochemistry*, vol. 47, pp. 819-846, Jul. 1978.

Telenius, H. et al., "Degenerate oligonucleotide-primed PCR: General amplification of target DNA by a single degenerate primer," *Genomics*, vol. 13, No. 3, pp. 718-725, Jul. 1992.

Wanunu, M. et al. "Chemically Modified Solid-State Nanopores," *Nano Letters*, 7(6), pp. 1580-1585, 2007.

Wu, X. et al, "Microfluidic differential resistive pulse sensors," *Electrophoresis*, 29(13), pp. 2754-2759, 2008.

Yan, X. et al, "Parallel Fabrication of Sub-50-nm Uniformly Sized Nanaparticles by Deposition through a Patterned Silicon Nitride Nanostencil," *Nano Letters*, 5(6), pp. 1129-1134, 2005.

Yang, J. et al. "Rapid and precise scanning helium ion microscope milling of solid-state nanopores for biomolecule detection," *Nanotechnology*, vol. 22, 6 pages, 2011.

Zhang, L. et al., "Whole genome amplification from a single cell: implications for genetic analysis," *Proc. Natl. Acad. Sci. USA*, vol. 89, No. 13, pp. 5847-5851, Jul. 1, 1992.

Zhe, J. et al, "A micromachined high throughput Coulter counter for bioparticle detection and counting," *J. Micromech. Microeng.*, vol. 17, pp. 304-313, 2007.

Hlawacek, G. "Helium Ion Microscopy," *Journal of Vacuum Sciences B*, 32:020801, 16 pages, Feb. 6, 2014.

Aksimentiev, A. et al., "Microscopic Kinetics of DNA Translocation through Synthetic Nanopores," *Biophysical Journal*, vol. 87, pp. 2086-2097. Sep. 2004.

Algar, W. R. et al. "Quantum dots as donors in fluorescence resonance energy transfer for the bioanalysis of nucleic acids, proteins, and other biological molecules," *Anal Bioanal Chem*, vol. 391, pp. 1609-1618. Jul. 2008.

Anderson, B.N. et al. "Probing Solid-State Nanopores with Light for the Detection of Unlabeled Analytes," *ACS Nano*, 8(11), pp. 11836-11845, Nov. 2014.

Anderson, J. et al. "Incorporation of reporter-labeled nucleotides by DNA polymerases," *Biotechniques*, 38(2): 257-263, Feb. 2005.

Anderson, M. et al, "Next Generation DNA Sequencing and the Future of Genomic Medicine," *Genes*, vol. 1, pp. 38-69, 2010.

Augustin, M.A. et al. "Progress towards single-molecule sequencing: enzymatic synthesis of nucleotide-specifically labeled DNA," *Journal of Biotechnology*, 86(3), pp. 289-301, Apr. 2001.

Australian Patent Application No. 2010301128 filed May 13, 2010 in the name of Huber, Office Action mailed Aug. 15, 2014.

Baker, L.A. et al., "A makeover for Membranes," *Nature Nanotechnology*, vol. 3, pp. 73-74, Feb. 2008.

Bayley, H., "Sequencing single molecules of DNA," *Current Opinion in Chemical Biology*, 10(6), pp. 628-637. Dec. 2006.

Begovich, A.B. et al., " A Missense Single-Nucleotide Polymorphism in a Gene Encoding a Protein Tyrosine Phosphatase

(56) References Cited

OTHER PUBLICATIONS (PTPN22) Is Associated with Rheumatoid Arthritis," *The American Journal of Human Genetics*, vol. 75, No. 2, pp. 330-337, Aug. 1, 2004.

Brakmann, S. "High-Density Labeling of DNA for Single Molecule Sequencing," *Methods in Molecular Biology*, vol. 283, pp. 137-144, Jun. 2004.

Brakmann, S. et al. "High-Density Labeling of DNA: Preparation and Characterization of the Target Material for Single-Molecule Sequencing," *Angew. Chem. Int. Ed.*, 40(8), pp. 1427-1429, Apr. 2001.

Branton, D. et al, "The potential and challenges of nanopore sequencing," *Nature Biotechnology*, 26(10), pp. 1146-1153, Oct. 2008.

Butler, T. Z. et al., "Single-molecule DNA detection with an engineered MspA protein nanopore," *Proceedings of the National Academy of Sciences*, 105(52), pp. 20647-20652, Dec. 30, 2008.

Chan, E. Y. et al. "DNA Mapping Using Microfluidic Stretching and Single-Molecule Detection of Fluorescent Site-Specific Tags," *Genome Research*, vol. 14, pp. 1137-1146, 2004.

Chan, WC. et al. "Quantum Dot Bioconjugates for Ultrasensitive Nonisotopic Detection," *Science*, vol. 281, pp. 2016-2018, Sep. 25, 1998.

Chansin et al. "Single-Molecule Spectroscopy Using Nanoporous Membranes," *Nano Letters*, vol. 7, No. 9; pp. 2901-2906, 2007.

Chen, P. et al, "Atomic Layer Deposition to Fine-Tune the Surface Properties and Diameters of Fabricated Nanopores," *Nano Letters*, 4(7), pp. 1333-1337, 2004.

Danelon, C. et al. "Fabrication and Functionalization of Nanochannels by Electron-Beam-Induced Silicon Oxide Deposition," *Langmuir*, vol. 22, pp. 10711-10715, 2006.

Deamer, et al., "Characterization of Nucleic Acids by Nanopore Analysis," *Acc. Chem. Res.*, 35(10), pp. 817-825, 2002.

Deamer, et al., "Nanopores and nucleic acids: prospects for ultrarapid sequencing," *Trends in Biotechnology*, 18(4), abstract only (2 pages), Apr. 1, 2000.

Dela Torre, R. et al. "Fabrication and Characterization of Solid-state Nanopore Arrays for High Throughput DNA Sequencing," *Nanotechnology*, 23(38), 12 pages, Sep. 28, 2012.

Dennis, A.M. et al., "Quantum Dot—Fluorescent Protein Pairs as Novel Fluorescence Resonance Energy Transfer Probes," *Nano Lett.*, vol. 8, No. 5, pp. 1439-1445, 2008, American Chemical Society.

Dorre, K. et al. "Highly efficient single molecule detection in microstructures," *Journal of Biotechnology*, 86(3), pp. 225-236, Apr. 2001.

Eid et al "Real-time DNA sequencing from single polymerase molecules," *Science*, 232: 133-138, Jan. 2, 2009 and Supplemental Material.

Eigen, M. et al. "Sorting single molecules: Application to diagnostics and evolutionary biotechnology," *Proc. Natl. Acad. Sci.*, vol. 91, pp. 5740-5747, Jun. 1994.

Etoh, et al. "An Image Sensor Which Captures 100 Consecutive Frames at 1000000 Frames/s," *IEEE Transactions on Electron Devices*, vol. 50. No. 1; pp. 144-151, Jan. 2003.

European Patent Application No. 10820963.6 filed May 13, 2010 in the name of Huber, Search Report and Opinion mailed Dec. 3, 2013.

Foldes-Papp, Z. et al. "Fluorescent high-density labeling of DNA: error-free substitution for a normal nucleotide," *Journal of Biotechnology*, 86(3), pp. 237-253. Mar. 2001.

Fologea, et al. "Detecting Single Stranded DNA with a Solid State Nanopore," *Nano Letters*, 5 (10), abstract only, Aug. 31, 2005.

Fontes, A. et al. "Quantum Dots in Biomedical Research," Biomedical Engineering—Technical Applications in Medicine, Chapter 12, pp. 269-290, Sep. 6, 2012.

Freeman, J. et al, "Profiling the T-cell receptor beta-chain repertoire by massively parallel sequencing," *Genome Research*, vol. 19, pp. 1817-1824, Jun. 2009.

Gierlich, J. et al, "Synthesis of Highly Modified DNA by a Combination of PCR with Alkyne-Bearing Triphosphates and Click Chemistry," *Chem. Eur. J.*, vol. 13, pp. 9486-9494, 2007.

Giller, G. et al. "Incorporation of reporter molecule-labeled nucleotides by DNA polymerases. I. Chemical synthesis of various reporter group-labeled 2'-deoxyribonucleoside-5'-triphosphates," *Nucleic Acids Research*, 31(10), pp. 2630-2635, May 2003.

Gu, L. et al, "Single molecule sensing by nanopores and nanopore devices," *Analyst*, 135(3), pp. 441-451, 2010.

Gupta, et al., "Single-molecule DNA sequencing technologies for future genomic research," *Trends in Biotechnology*, 26(11), pp. 602-611, Nov. 1, 2008.

Hall, A. R. et al. "Hybrid pore formation by directed insertion of alpha hemolysin into solid-state nanopores," *Nature Nanotechnology*, 5(12), pp. 874-877, Dec. 2010.

He, H. et al., "Single Nonblinking CdTe Quantum Dots Synthesized in Aqueous Thiopropionic Acid,"*Angew. Chem. Int. Ed.* vol. 45, pp. 7588-7591, Oct. 2006.

Heins, E.A. et al., "Detecting Single Porphyrin Molecules in a Conically Shaped Synthetic Nanopore," *Nano Letters*, 5(9), pp. 1824-1829, Jul. 26, 2005, Supporting Information.

Heintzmann, R. et al., "Breaking the resolution limit in light microscopy," *Briefings in Functional Genomics and Proteomics*, 5(4), pp. 289-301, Dec. 2006.

Hemminger, "Visualizing and Understanding Complex MicrolNanonuidic Flow Behavior," Dissertation, the Ohio State University, 2010, available online at <http://etd.ohiolink.edulsend•pdf.cgUHemminger%200rin%20L.pdf?osu1275398565>.

Holt, R. et al, "The new paradigm of flow cell sequencing," *Genome Research*, vol. 18, pp. 839-846, 2008.

Huang, S. et al. "High-throughput optical sensing of nucleic acids in a nanopore array," *Nature Nanotechnology*, vol. 10, pp. 986-991, Aug. 2015.

Ivankin, A. et al. "Label-Free Optical Detection of Biomolecular Translocation through Nanopore Arrays," *ACS Nano*, 8(10), pp. 10774-10781, Sep. 2014.

Japanese Patent Application No. 2012-532069 filed May 13, 2010 in the name of Huber, Final Office Action mailed Apr. 17, 2015.

Japanese Patent Application No. 2012-532069 filed May 13, 2010 in the name of Huber, Office Action mailed Aug. 1, 2014.

Japanese Patent Application No. 2014-224165 filed May 13, 2010 in the name of Huber, Office Action mailed Oct. 15, 2015.

Johansson, MK et al. "Choosing Reporter-Quencher Pairs for Efficient Quenching Through Formation of Intramolecular Dimers," *Methods in Molecular Biology*, vol. 335:2, pp. 17-29, 2006.

Johansson, MK et al. "Intramolecular Dimers: A New Design Strategy for Fluorescence-Quenched Probes," *Chem. Eur. J.*, 9, 3466-3471, Jul. 2003.

Kang, X. et al., "A storable encapsulated bilayer chip containing a single protein nanopore,"..7 *Am Chem Soc.* vol. 129, No. 15, pp. 4701-4705, Mar. 22, 2007.

Keyser, U. F. "Controlling molecular transport through nanopores," *Journal of the Royal Society Interface*, 10 page, published online 2011.

Kircher et al "High-throughput DNA sequencing-concepts and limitations," *Bioessays*, vol. 32, pp. 524-536, 2010.

Kleefen. A. et al. "Multiplexed Parallel Single Transport Recordings on Nanopore Arrays," *Nano Letters*,vol. 10, pp. 5080-5087, 2010.

Kocer, A. et al. "Nanopore sensors: From hybrid to abiotic systems," *Biosensors and Bioelectronics*, vol. 38, 10 pages, 2012.

Kolb, H. et al, "Click Chemistry: Diverse Chemical Function from a Few Good Reactions," *Angew. Chem. Int. Ed.*, vol. 40, pp. 2005-2021, 2001.

Kristensen, V. N. et al., "High-Throughput Methods for Detection of Genetic Variation," *BioTechniques*, 30(2), pp. 318-332, Feb. 2001.

Lerner, H. et al "Prospects for the Use of Next-Generation Sequencing Methods in Ornithology," *The Auk*, 127(1), pp. 4-15, 2010.

Levene et al, "Zero mode waveguide for single-molecule analysis in high concentration," *Science*, 299: 682-686, Jan. 31, 2003.

Li et al., "DNA Molecules and Configurations in a Solid-State Nanopore Microscope," *Nat. Mater*, vol. 2, pp. 611-615, Sep. 2003.

(56) References Cited

OTHER PUBLICATIONS

Lin, B. et al., "Recent Patents and Advances in the Next-Generation Sequencing Technologies," *Recent Patents on Biomedical Engineering*, vol. 1, No. 1, pp. 60-67, 2008, Benthan Science Publishers Ltd.

Luan et al., "Slowing and controlling the translocation of DNA in a solid-state nanopore," *Nanoscale*, 4(4): 1068-1077, Feb. 21, 2012.

Maitra, R. D. et al. "Recent advances in nanopore sequencing," *Electrophoresis*, vol. 33, pp. 3418-3428, 2012.

Marras, S. "Interactive Fluorophore and Quencher Pairs for Labeling Fluorescent Nucleic Acid Hybridization Probes," *Mol Biotechnol*, vol. 38, 247-255, Mar. 2008.

Marras, S. "Selection of Fluorophore and Quencher Pairs for Fluorescent Nucleic Acid Hybridization Probes," *Methods in Molecular Biology*, vol. 335, 3-16, 2006.

Meagher, R. J. et al. "Free-solution electrophoresis of DNA modified with drag-tags at both ends," *Electrophoresis*, vol. 27, pp. 1702-1712, 2006.

Meagher, R. J. et al. "Sequencing of DNA by Free-Solution Capillary Electrophoresis Using a Genetically Engineered Protein Polymer Drag-Tag," *Anal. Chem.*, vol. 80, pp. 2842-2848, Apr. 15, 2008.

Medintz, I.L. et al. "A fluorescence resonance energy transfer-derived structure of a quantum dot-protein bioconjugate nonassembly," *PNAS*, 101(26), pp. 9612-9617. Jun. 29, 2004.

Medintz, I.L. et al. "Quantum dot bioconjugates for imaging, labelling and sensing," *Nature Materials*, vol. 4, 435-446, Jun. 2005.

Meller, A. et al., "Rapid nanopore discrimination between single polynucleotide molecules," *The National Academy of Sciences*, 2000, 7 pages.

Meller, A. et al., "Voltage-Driven DNA Translocations through a Nanopore," *Phys. Rev. Lett.* 86(15), pp. 3435-3438, Apr. 2001.

Meller, et al., "Single Molecule Measurements of DNA Transport through a Nanopore," *Electrophoresis*, vol. 23, pp. 2583-2591, 2002.

Metzker, M. "Sequencing technologies—the next generation," *Nature Review Genetics*, vol. 11, pp. 31-46, Jan. 2010.

Meyers, R. "Molecular Biology and Biotechnology, A Comprehensive Desk Reference," VCH Publisher, Inc., New York, NY, 1995, pp. 317-319.

Mir, K., "Ultrasensitive RNA profiling: Counting single molecules on microarrays," *Genome Research*, 16:1195-1197, Oct. 2006.

Moerner, W.E. et al. "Methods of single-molecule fluorescence spectroscopy and microscopy," *Review of Scientific Instruments*, 74(8), pp. 3597-3619, Aug. 2003.

Ogura, Y. et al., "A Frameshift Mutation in NOD2 Associated with Susceptibility to Crohn's Disease," *Nature*, vol. 411, pp. 603-606, May 31, 2001, Macmillan Magazine Ltd.

Paul N. et al "PCR incorporation of modified dNTPs: the substrate properties of biotinylated dNTPs," *Biotechniques*, 48(4), 333-334, Apr. 2010.

PCT International Patent Application No. PCT/US2010/034809 filed May 13, 2010 in the name of Huber, International Search Report and Written Opinion mailed Feb. 6, 2014.

PCT International Patent Application No. PCT/US2010/034809 filed May 13, 2010 in the name of Huber, International Search Report and Written Opinion mailed Sep. 13, 2010.

PCT International Patent Application No. PCT/US2011/54365 filed Sep. 30, 2011 in the name of Huber et al., International Search Report and Written Opinion mailed Apr. 25, 2012.

PCT International Patent Application No. PCT/US2013/067126 filed Oct. 28, 2013 in the name of Huber, International Search Report and Written Opinion mailed May 6, 2014.

PCT International Patent Application No. PCT/US2014/039444 filed May 23, 2014 in the name of Huber et al., International Search Report and Written Opinion mailed Dec. 3, 2014.

PCT International Patent Application No. PCT/US2015/054756 filed Oct. 8, 2015 in the name of Huber et al., International Search Report and Written Opinion mailed Jan. 6, 2016.

PCT International Patent Application No. PCT/US2015/057245 filed Oct. 23, 2015 in the name of Huber et al., International Preliminary Report on Patentability mailed Nov. 15, 2016.

PCT International Patent Application No. PCT/US2015/057245 filed Oct. 23, 2015 in the name of Huber et al., International Search Report and Written Opinion mailed Jan. 21, 2016.

Ramachandran, G. et al. "Current bursts in lipid bilayers initiated by colloidal quantum dots," *Applied Physics Letter*, 86:083901-1 to 083901-3, Feb. 17, 2005.

Ramsay, N. et al. "CyDNA: Synthesis and Replication of Highly Cy-Dye Substituted DNA by an Evolved Polymerase," *J. Am. Chem. Soc.*, vol. 132, 5096-5104, Mar. 2010.

Randolph, JB et al. "Stability, specificity and fluorescence brightness of multiply-labeled fluorescent DNA probes," *Nucleic Acids Research*, 25(14) 2923-2929, May 1997.

Reed, M.A. "Quantum Dots," *Scientific American*, pp. 118-123, Jan. 1993.

Resch-Genger, U. et al. "Quantum dots versus organic dyes as fluorescent labels," *Nature Methods*, 5(9), pp. 763-775. Sep. 2008.

Rhee, M. et al., "Nanopore Sequencing Technology: research trends and applications," *Trends in Biotechnology*, vol. 24, No. 12, pp. 580-586. Dec. 2006.

Roy et al. "A practical guide to single molecule FRET," *Nature Methods*, 5(6): 507-516, Jun. 2008.

Sabanayagam, C.R. et al., "Long time scale blinking kinetics of cyanine fluorophores conjugated to DNA and its effect on Forster resonance energy transfer," *J. Chem. Phys.*, 123(22), pp. 224708-1-224708-7, Dec. 2005.

Sanger, F. et al., "DNA Sequencing with Chain-Terminating Inhibitors," *Proc. Natl. Acad. Sci. USA*, vol. 74, No. 12, pp. 5463-5467, Dec. 1977.

Sauer, M. et al. "Single molecule DNA sequencing in submicrometer channels: state of the art and future prospects," *Journal of Biotechnology*, 86(3), 181-201, Apr. 2001.

Seela, F. et al. "Fluorescent DNA: the development of 7-deazapurine nucleoside triphosphates applicable for sequencing at the single molecule level," *Journal of Biotechnology*, 86(3), 269-279, Apr. 2001.

Shaffer, C., "Next generation sequencing outpaces expectations," *Nature Biotechnology*, vol. 25, p. 149, Feb. 2007.

Shi, L. et al. "Luminescent Quantum Dots Fluorescence Resonance Energy Transfer-Based Probes for Enzymatic Activity and Enzyme Inhibitors," *Anal. Chem*, 79(1), pp. 208-214, Jan. 1, 2007.

Smolina, I.V. et al. "High-density fluorescently labeled rolling-circle amplicons for DNA diagnostics," Analytical Biochemistry, 347: 152-155, Jun. 21, 2005.

Soni, et al. "Progress toward Ultrafast DNA Sequencing Using Solid•State Nanopores," *Clinical Chemistry*, vol. 53, No. 11; pp. 1996-2001, 2007.

Soni, G. V. et al. "Synchronous optical and electrical detection of biomolecules traversing through solid-state nanopores," *Review of Scientific Instruments*, pp. 014301-1-014301-7, published online Jan. 19, 2010.

Stephan, J. et al. "Towards a general procedure for sequencing single DNA molecules," *Journal of Biotechnology*, 86(3) 255-267, Apr. 2001.

Strittmatter, W.J. et al, "Apolipoprotein E and Alzheimer's Disease," *Annual Review of Neuroscience*, vol. 19, pp. 53-77, 1996.

Stryer, L. et al. "Diffusion-enhanced fluorescence energy transfer," *Annual review of biophysics and bioengineering*, vol. 11. No. 1; pp. 203-222, 1982.

Tamura, T., *Molecular Biology Illustrated*, revised Second Edition, pp. 174-175, Jan. 1, 2003.

Tasara, T. et al. "Incorporation of reporter molecule-labeled nucleotides by DNA polymerases. II. High-density labeling of natural DNA," *Nucleic Acids Research*, 31(10), 2636-2646, May 2003.

Thompson, J. F. et al. "The properties and applications of single-molecule DNA sequencing," *Genome Biology*, 12(217), 10 pages, 2011.

Timp, W., et al, "DNA base-calling form a nanopore using a Viterbi algorithm," *Biophysical J.*, vol. 102, pp. L37-L39, May 2012.

(56) References Cited

OTHER PUBLICATIONS

Tucker, T. et al, "Massively Parallel Sequencing: The Next Big Thing in Genetice Medicine," *Am. J. Human Genet.*, vol. 85, pp. 142-154, Aug. 2009.
Turner, E. et al, "Methods for Genomic Partitioning," *Annual Review of Genomics and Human Genetics*, vol. 10, pp. 263-284, 2009.
U.S. Appl. No. 13/426,515 filed Mar. 21, 2012 in the name of Huber, Non-final Office Action mailed Dec. 2, 2013.
U.S. Appl. No. 13/426,515 filed Mar. 21, 2012 in the name of Huber, Notice of Allowance mailed Apr. 11, 2014.
U.S. Appl. No. 13/662,532 filed Oct. 28, 2012 in the name of Huber, Final Office Action mailed Mar. 17, 2015.
U.S. Appl. No. 13/662,532 filed Oct. 28, 2012 in the name of Huber, Non-final Office Action mailed Aug. 7, 2014.
U.S. Appl. No. 13/662,532 filed Oct. 28, 2012 in the name of Huber, Non-final Office Action mailed Dec. 20, 2013.
U.S. Appl. No. 14/018,376 filed Sep. 4, 2013 in the name of Huber, Final Office Action mailed Sep. 24, 2015.
U.S. Appl. No. 14/018,376 filed Sep. 4, 2013 in the name of Huber, Non-final Office Action mailed Mar. 3, 2015.
U.S. Appl. No. 14/285,474 filed May 22, 2014 in the name of Huber, Non-final Office Action mailed Apr. 30, 2015.
U.S. Appl. No. 14/285,474 filed May 22, 2014 in the name of Huber, Notice of Allowance mailed Nov. 20, 2015.
U.S. Appl. No. 61/168,431 filed Apr. 10, 2009.
Venkatesan, B. M. et al. "Lipid bilayer coated Al2O3 naopore sensors: towards a hybrid biological solid-state nanopore," *Biomed Microdevices*, 13(4), 21 pages, 2011.
Venkatesan, B. M. et al. "Nanopore sensors for nucleic acid analysis," *Nature Nanotechnology*, vol. 6, pp. 615-624, Oct. 2011.
Vercoutere, W. et al., "Rapid discrimination among individual DNA hairpin molecules at single-nucleotide resolution using an ion channel," *Nature Biotechnology*, vol. 19, pp. 248-252, Mar. 2001.
Voelkerding, K. et al, "Next-Generation Sequencing: From Basic Research to Diagnostic," *Clinical Chemistry*, 55:4, pp. 641-658, 2009.
Walker, B. et al. "Key Residues for Membrane Binding, Oligomerization, and Pore Forming Activity of Staphylococcal alpha-Hemolysin Identified by Cysteine Scanning Mutagenesis and Targeted Chemical Modification," *Journal of Biological Chemistry*, 270(39), pp. 23065-23071, Sep. 29, 1995.
Wang, H. et al., "Nanopores with a spark for single-molecule detection," *Nature Biotechnology*, vol. 19, pp. 622-633, Jul. 2001.
Wanunu, M. et al."Nanopores: A journey towards DNA sequencing," *Physics of Life Reviews*, vol. 9, pp. 125-158, 2012.
White et al., "Single Ion-Channel Recordings Using Glass Nanopore Membranes," *J. Amer. Chem. Soc.*, 129:11766-11775, Sep. 5, 2007.
Won, J. et al. "Protein polymer drag-tags for DNA separations by end-labeled free solution electrophoresis," *Electrophoresis*, vol. 26, pp. 2138-2148, 2005.
Xu, et al., "Perspectives and Challenges of Emerging Single-Molecule DNA Sequencing Technologies," *SMALL*, 5(53), pp. 2638-2649, Dec. 4, 2009.
Yu, H. et al. "Cyanine dye dUTP analogs for enzymatic labeling of DNA probes," *Nucleic Acids Research*, 22(15), 3226-3232, Apr. 1994.
Yu, Y. et al. "Facile preparation of non-self-quenching fluorescent DNA strands with the degree of labeling up to the theoretic limit," *Chem. Commun.*, vol. 48, 6360-6362, May 2012.
Zheng, S. et al. "Parallel analysis of biomolecules on a microfabricated capillary array chip," *Electrophoresis*, vol. 26, abstract only, Mar. 2006.
Zhu, Z. et al. "Directly labeled DNA probes using fluorescent nucleotides with different length linkers," *Nucleic Acids Research*, 22(16), 3418-3422, Aug. 1994.
Zwolak, M. et al., "Colloquium: Physical approaches to DNA sequencing and detection," *Reviews of Modern Physics*, 80(1), pp. 141-165, Jan. 2, 2008.

* cited by examiner

FRET

No FRET

FRET

No FRET

FRET

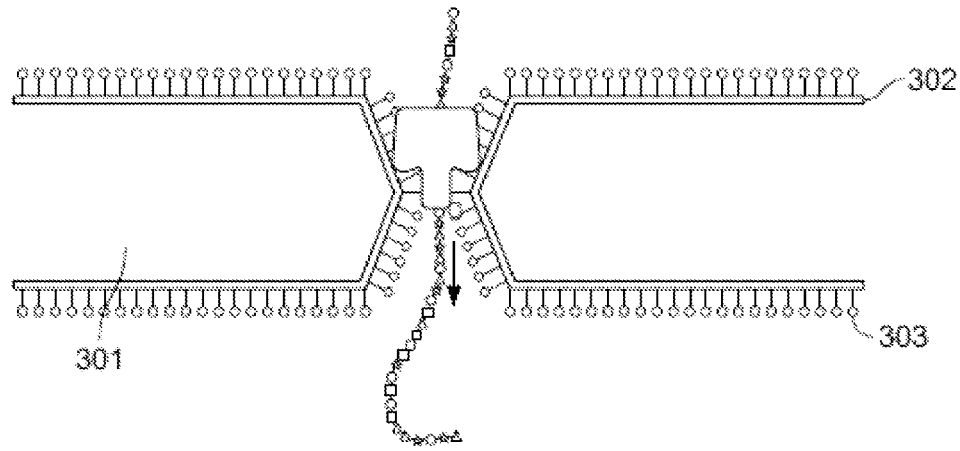
Fig. 3B
Figure 4A
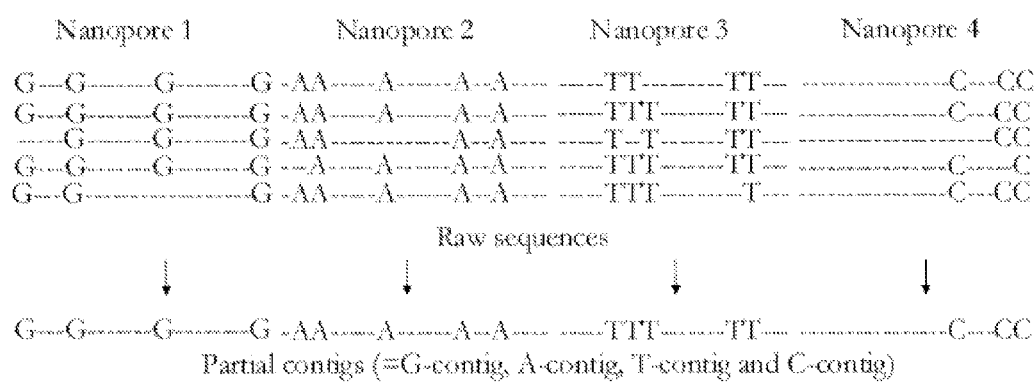

Quenching

No Quenching

REDUCING BACKGROUND FLUORESCENCE IN MEMS MATERIALS BY LOW ENERGY ION BEAM TREATMENT

CROSS-REFERENCE TO RELATED APPLICATION

This application is a continuation of International Patent Application No. PCT/US2013/067126 filed Oct. 28, 2013, which is a continuation-in-part of U.S. patent application Ser. No. 13/662,532 filed Oct. 28, 2012 and which also claims the benefit of priority to U.S. Provisional Patent Application No. 61/819,606 filed May 5, 2013, each of which is incorporated herein by reference in its entirety.

BACKGROUND

The ability to fabricate analytical devices at micrometer and nanometer scales has enabled measurement and monitoring of many physical, chemical and biological parameters unobtrusively, inexpensively and with great accuracy, e.g. Grayson et al, Proceedings IEEE, 92(1): 6-21 (2004); Schumacher et al, Lab Chip, 12(3): 464-473 (2012); and the like. Such devices may be fabricated in wide variety of substrate materials (referred to herein as microelectromechanical system materials, or "MEMS materials") which are typically selected on the basis of application-specific requirements, such as, chemical inertness, strength, rigidity, conductive or insulation properties, temperature sensitivity, ease and expense of fabrication, and the like. In analytical devices where optically based sensing or manipulation is employed, the absence of, or at least the controllability of, optical activity in substrate materials is important.

Optical detection of nucleotides has been proposed as a potential solution to some of the technical difficulties in the field of nanopore sequencing, e.g. Huber, International patent publication WO 2011/040996; Russell, U.S. Pat. No. 6,528,258; Pittaro, U.S. patent publication 2005/0095599; McNally et al, Nano Lett., 10: 2237-2244 (2010); and the like. Nanopore sequencing relies heavily on the use of micro- and nanofabricated MEMS materials, whether nucleotide detection is optically based or current based. Unfortunately, although many MEMS materials meet chemical, strength, rigidity and other requirements for nanopore sequencing and other analytical processes, they may be optically active. That is, they may generate a high level of background fluorescence that obscures the very low level high frequency fluorescent signals characteristic of optically based nanopore sequencing and other optically based measurements.

In view of the above, it would be advantageous to analytical devices comprising MEMS materials and optical detection systems, such as nanopore sequencing devices, if there was a method available for reducing or eliminating their optical activity, such as the undesired generation of background fluorescence.

SUMMARY OF THE INVENTION

Methods for fabricating materials useful for optical detection in microfluidic and nanofluidic devices, such as those used in nanopore-based nucleic acid sequencing are described herein.

In certain variations, a method of reducing background fluorescence in a MEMS material comprises the step of treating a surface of the MEMS material with a low energy ion beam.

Variations or embodiments are exemplified in a number of implementations and applications, some of which are summarized below and throughout the specification.

BRIEF DESCRIPTION OF THE DRAWINGS

FIG. 3B illustrates one embodiment of a hybrid nanopore where the surface of the solid state membrane (301) coated with a hydrophobic layer (302) to which a lipid layer is adhered (303). The lipids forms a gigaohm seal with the inserted pore protein.

FIG. 4A illustrates partial contigs from nucleic acid sequencing utilizing a singly labeled nucleic acid.

DETAILED DESCRIPTION OF THE INVENTION

Figure 1A:
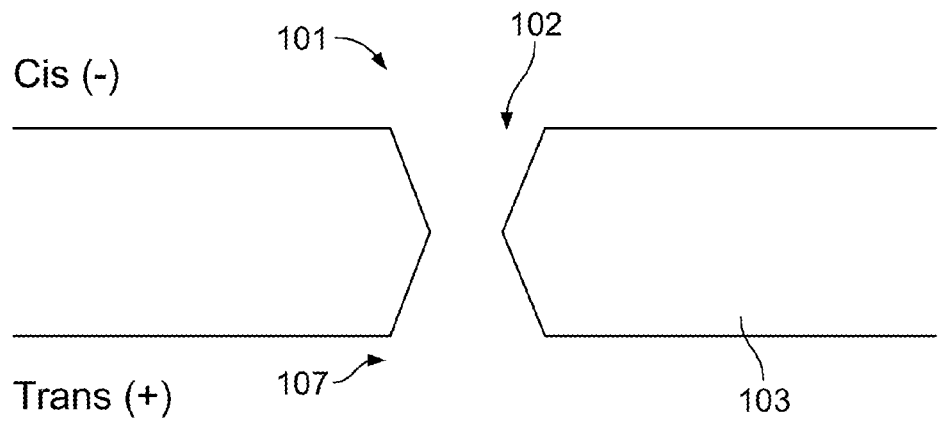
FIGS. 1A-1C illustrate one embodiment of a hybrid biosensor.

In one variation, a method of treating a MEMS material with a low energy ion beam to reduce or eliminate background fluorescence is provided. Typically such treatment is carried out by directing an ion beam to a surface region of the MEMS material, at a sufficiently high energy to cause a physical change in the MEMS material at its surface or near its surface to disrupt or inactivate structures contributing to autofluorescence, but not with such high energy that melting, vaporization, significant deformations or sputtering occur. The minimal energy required may be readily determined on a material-by-material basis by gradually increasing beam energy starting from zero and measuring reduction in autofluorescence with increasing beam energy. As used herein, the term "autofluorescence" is used synonymously with "background fluorescence" to mean fluorescence emanating from a source at or near a surface of a MEMS material upon excitation with a light source selected to excite a fluorescent label that is not a part of the MEMS material. Thus, autofluorescence in a MEMS material depends on the frequency of the light source. In one aspect, the frequency of the light source is selected to excite organic fluorescent dyes, so that a method as described herein reduces autofluorescence of frequencies in the visible range of light as well as frequencies from the near infrared to the near ultraviolet.

MEMS materials include a wide variety of solids capable of microfabrication and use in analytical techniques using optical detection. Exemplary MEMS materials are silicon-based substrates, such as silicon nitride and silicon dioxide or metal based substrates, such as aluminum oxide. In one aspect, MEMS materials are processed and used in the form of a membrane. In one embodiment, the MEMS material is silicon nitride.

A wide variety of focused ion beams may be employed in the variations or methods described herein and guidance for the production and application of such beams at various energies may be found in such references as, Natasi et al, Ion Solid Interactions: Fundamentals and Applications (Cambridge University Press, 1996), and like references. Exemplary focused ion beams include helium ion beams, neon ion beams and gallium ion beams. In one embodiment, a helium ion beam is used in the methods described herein. Helium ion beams may be produced with a commercially available ion beam microscope (HIM) (e.g. Zeiss Orion Nanofab).

Beam configuration and its application to a MEMS material surface may vary widely. Beam configuration includes beam width or cross section and energy delivered per unit area. Beams may be directed to MEMS material surface to form disjoint surface patches of bleaching or to form continuous areas of bleaching, or both approaches may be used in device fabrication.

Nanopore Sequencing

An important application of the variations or methods described herein is the bleaching of certain MEMS materials to facilitate their use in optically based nanopore sequencing, or other analytical processes. Nanopores for such processes may be fabricated in a variety of MEMS materials including but not limited to, silicon nitride ($Si_3N_4$), silicon dioxide ($SiO_2$), and the like. The fabrication and operation of nanopores for analytical applications, such as DNA sequencing, are disclosed in the following exemplary references that are incorporated by reference: Feier, U.S. Pat. No. 4,161,690; Ling, U.S. Pat. No. 7,678,562; Hu et al, U.S. Pat. No. 7,397,232; Golovchenko et al, U.S. Pat. No. 6,464,842; Chu et al, U.S. Pat. No. 5,798,042; Sauer et al, U.S. Pat. No. 7,001,792; Su et al, U.S. Pat. No. 7,744,816; Church et al, U.S. Pat. No. 5,795,782; Bayley et al, U.S. Pat. No. 6,426,231; Akeson et al, U.S. Pat. No. 7,189,503; Bayley et al, U.S. Pat. No. 6,916,665; Akeson et al, U.S. Pat. No. 6,267,872; Meller et al, U.S. patent publication 2009/0029477; Howorka et al, International patent publication WO2009/007743; Brown et al, International patent publication WO2011/067559; Meller et al, International patent publication WO2009/020682; Polonsky et al, International patent publication WO2008/092760; Van der Zaag et al, International patent publication WO2010/007537; Yan et al, Nano Letters, 5(6): 1129-1134 (2005); Iqbal et al, Nature Nanotechnology, 2: 243-248 (2007); Wanunu et al, Nano Letters, 7(6): 1580-1585 (2007); Dekker, Nature Nanotechnology, 2: 209-215 (2007); Storm et al, Nature Materials, 2: 537-540 (2003); Wu et al, Electrophoresis, 29(13): 2754-2759 (2008); Nakane et al, Electrophoresis, 23: 2592-2601 (2002); Zhe et al, J. Micromech. Microeng., 17: 304-313 (2007); Henriquez et al, The Analyst, 129: 478-482 (2004); Jagtiani et al, J. Micromech. Microeng., 16: 1530-1539 (2006); Nakane et al, J. Phys. Condens. Matter, 15 R1365-R1393 (2003); DeBlois et al, Rev. Sci. Instruments, 41(7): 909-916 (1970); Clarke et al, Nature Nanotechnology, 4(4): 265-270 (2009); Bayley et al, U.S. patent publication 2003/0215881; and the like. Briefly, in one aspect, a 1-50 nm channel is formed through a substrate, usually a membrane, through which an analyte, such as DNA, is induced to translocate. The solid-state approach of generating nanopores offers robustness and durability as well as the ability to tune the size and shape of the nanopore, the ability to fabricate high-density arrays of nanopores on a wafer scale, superior mechanical, chemical and thermal characteristics compared with lipid-based systems, and the possibility of integrating with electronic or optical readout techniques. Biological nanopores on the other hand show an atomic level of precision that cannot yet be replicated by the semiconductor industry. In addition, established genetic techniques (notably site-directed mutagenesis) can be used to tailor the physical and chemical properties of the biological nanopore. However, each system has significant limitations: Protein nanopores rely on delicate lipid bilayers for mechanical support, and the fabrication of solid-state nanopores with precise dimensions remains challenging. Combining solid-state nanopores with a biological nanopore overcomes some of these shortcomings, especially the precision of a biological pore protein with the stability of a solid state nanopore. For optical read out techniques a hybrid nanopore also guarantees a precise location of the nanopore which simplifies the data acquisition greatly. The lateral diffusion of nanopore proteins inserted in a lipid bilayer makes an optical detection challenging. Since the biological part of a hybrid nanopore does not rely on the insertion in a lipid bilayer the degrees of freedom for modifications made to such a protein are greatly increased e.g. a genetically modified nanopore protein that does not spontaneously insert in a lipid bilayer may still be used as a protein component of a hybrid nanopore. Bilayer destabilizing agents such as quantum dots may be used to label a protein component of a hybrid nanopore.

In one variation, a device for detecting an analyte comprises the following elements; (a) a solid phase membrane separating a first chamber and a second chamber, the solid phase membrane having at least one aperture connecting the first chamber and the second chamber through a bore, and the solid phase membrane having been treated with a low energy ion beam to bleach its autofluorescence; and (b) a first member of a fluorescent resonance energy transfer (FRET) pair attached to the at least one aperture, so that whenever an analyte having at least one second member of the FRET pair attached thereto traverses the bore, the second member passes with a FRET distance of the first member of the FRET pair.

In another variation, a device for detecting an analyte comprises the following elements; (a) a solid phase membrane separating a first chamber and a second chamber, the solid phase membrane having at least one aperture connecting the first chamber and the second chamber, and having a hydrophobic coating on at least one surface, the solid phase membrane further having been treated with a low energy ion beam to bleach its autofluorescence; (b) a lipid layer disposed on the hydrophobic coating; (c) a protein nanopore immobilized in the aperture, the protein nanopore having a bore and interacting with the lipid layer to form a seal with the solid phase membrane in the aperture so that fluid communication between the first chamber and the second chamber occurs solely through the bore of the protein nanopore; and wherein the solid phase membrane or the protein nanopore has attached thereto at least one first member of a fluorescent resonance energy transfer (FRET) pair, so that whenever an analyte having at least one second member of the FRET pair attached thereto traverses the bore, the second member passes with a FRET distance of the first member of the FRET pair. In some embodiments, the hydrophobic coating is optional in that the surface of the solid phase membrane is sufficiently hydrophobic itself so that a lipid layer adheres to it stably. The at least one aperture will have an inner surface, or wall, connected to, or contiguous with the surfaces of the solid phase membrane. In some embodiments, the at least one aperture will be a plurality of apertures, and the plurality of apertures may be arranged as a regular array, such as a rectilinear array of apertures, the spacing of which depending in part on the number and kind of FRET pairs employed and the optical detection system used. Each of the apertures has a diameter, which in some embodiments is such that a protein nanopore is substantially immobilized therein. In some embodiments, substantially immobilized means that a protein nanopore may move no more than 5 nm in the plane of the solid phase membrane relative to the wall of the aperture. In another embodiment, substantially immobilized means that a protein nanopore may move no more than 5 nm in the plane of the solid phase membrane relative to the wall of the aperture. The protein nanopores each have a bore, or passage, therethrough which permit fluid communication between the first and second chambers when the protein nanopore is immobilized in an aperture. Generally, the bore is coaxially aligned with the aperture. One function of the hydrophobic layer is to provide a surface to retain lipids in and/or immediately adjacent to the at least one aperture. Such lipids, in turn, permit disposition and immobilization of a protein nanopore within an aperture in a functional conformation and in a manner that forms a fluid seal with the wall of the aperture. In some embodiments, such seal also prevents electrical current passing between the first and second chambers around the protein nanopore. For convenience of manufacture, in some embodiments the hydrophobic coating will be on one surface of the solid phase membrane and the wall(s) of the aperture(s).

Figure 1B:
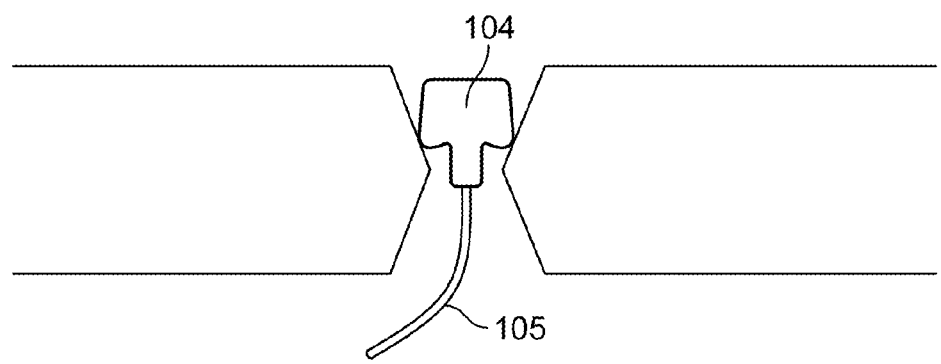
Figure 1C:
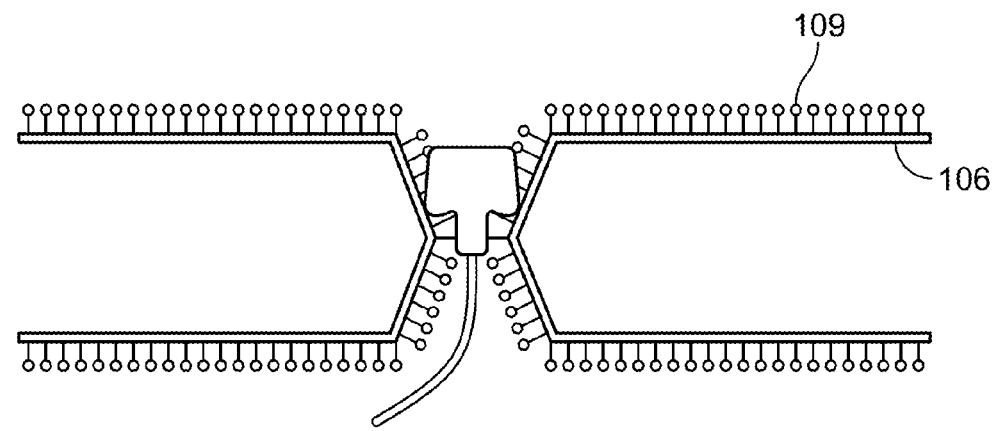

FIGS. 1A-1C are schematic diagrams of hybrid biosensors. A nanometer sized hole (102) is drilled into a solid-state substrate, or solid phase membrane, (103) which separates two chambers, or compartments cis (101) and trans (107). A protein biosensor (e.g a protein nanopore) (104) attached to a charged polymer (105), such as a single stranded DNA, is embedded into the solid-state nanohole by electrophoretic transport. In FIG. 1C the protein biosensor is inserted. In a nanometer sized hole which surface has a hydrophobic coating (106) and a lipid layer (109) attached thereto.

Figure 1D:
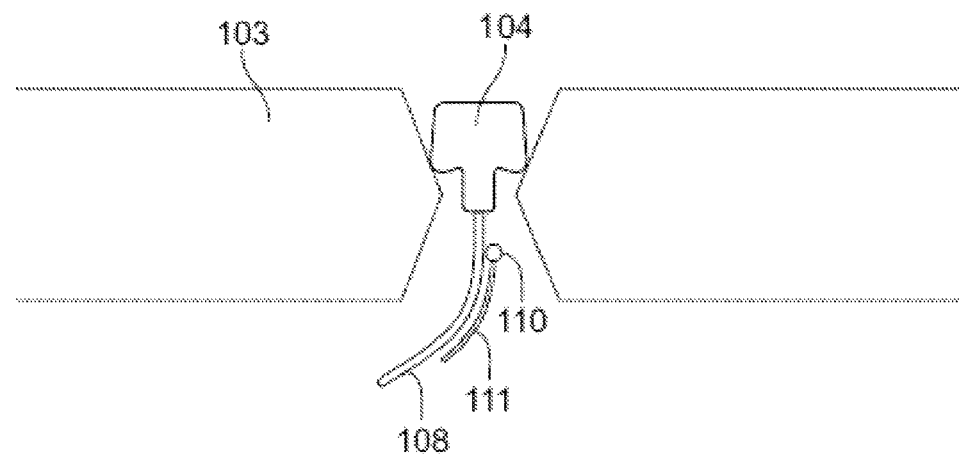
FIG. 1D illustrates an embodiment of a device with positioning of a member of a FRET pair using oligonucleotide hybridization.

FIG. 1D shows protein nanopore (104) inserted into an aperture drilled in a solid state membrane (103). Attached to the protein nanopore (104) is an oligonucleotide (108) to which a complementary secondary oligonucleotide (111) is hybridized. Said secondary oligonucleotide (111) has one or more second members of a FRET pair (110) attached to it.

Certain variations or embodiments described herein refer to the design and production of a hybrid biosensor used in optical nanopore sequencing, which consist of a solid-state orifice into which a protein biosensor, such as a protein nanopore, is stably inserted. A protein nanopore (e.g. alpha hemolysin) is attached to a charged polymer (e.g. double stranded DNA) which serves as a drag force in an applied electric field. In some embodiments, the aperture in the solid-state substrate is selected to be slightly smaller than the protein, thereby preventing it from translocating through the aperture. Instead, the protein will be embedded into the solid-state orifice. The solid-state substrate can be modified to generate active sites on the surface that allow the covalent attachment of the plugged-in protein biosensor resulting in a stable hybrid biosensor.

The polymer attachment site in the biosensor can be generated by protein engineering e.g. a mutant protein can be constructed that will allow the specific binding of the polymer. As an example, a cysteine residue may be inserted at the desired position of the protein. The cysteine can either replace a natural occurring amino acid or can be incorporated as an addition amino acid. Care must be taken not to disrupt the biological function of the protein. The terminal primary amine group of a polymer (i.e. DNA) is then activated using a hetero-bifunctional crosslinker (e.g. SMCC). Subsequently, the activated polymer is covalently attached to the cysteine residue of the protein biosensor.

In a preferred embodiment the attachment of the polymer to the biosensor is reversible. By implementing a cleavable crosslinker, an easily breakable chemical bond (e.g. an S—S bond) is introduced and the charged polymer may be removed after insertion of the biosensor into the solid-state aperture.

For someone skilled in the art it is obvious that a wide variety of different approaches for covalent or non-covalent attachment methods of a charged polymer to the protein biosensor are possible and the above described approach merely serves as an example. The skilled artisan will also realize that a variety of different polymers may be used as a drag force, including, but not limited to, single or double stranded DNA, polyethyleneglycol (PEG), polyvinylpyrrolidone (PVP), poly-L-lysine, linear polysaccharides etc. It is also obvious that these polymers may exhibit either a negative (−) or positive (+) charge at a given pH and that the polarity of the electric field may be adjusted accordingly to pull the polymer-biosensor complex into a solid-state aperture.

In a preferred embodiment, a donor fluorophore is attached to the protein nanopore. This complex is then inserted into a solid-state aperture or nanohole (3-10 nm in diameter) by applying an electric field across the solid state nanohole until the protein nanopore is transported into the solid-state nanohole to form a hybrid nanopore. The formation of the hybrid nanopore can be verified by (a) the inserting protein nanopore causing a drop in current based on a partial blockage of the solid-state nanohole and by (b) the optical detection of the donor fluorophore.

Once stable hybrid nanopores have formed single stranded, fluorescently labeled DNA is added to the cis chamber (the chamber with the (+) electrode). The applied electric field forces the negatively charged ssDNA to translocate through the hybrid nanopore during which the labeled nucleotides get in close vicinity of the donor fluorophore.

Energy may be transferred from the excited donor label to the acceptor label of the monomer as, after, while or before the labeled monomer exits, passes through or enters the hybrid nanopore. Energy emitted by the acceptor label as a result of the energy transfer may be detected, where the energy emitted by the acceptor label may be associated with a single or particular monomer (e.g., a nucleotide) of a biological polymer. The sequence of the biological polymer may then be deduced or sequenced based on the detection of the emitted energy from the monomer acceptor label which allows for the identification of the labeled monomer.

Methods for drilling solid state nanopores are described herein. A solid-state orifice is drilled into a nanometer thick supporting material such as, but not limited to silicon nitride, silicon oxide, aluminum oxide, graphene or thin metal membranes. The drilling is accomplished by focusing a high energy electron or ion beam onto the surface as established for instance in transmission electron microscopy (TEM). Such high energy electron or ion beams can easily be focused to the width of most protein-based biosensors. The size of the aperture drilled into the solid state material is on the order of 1-500 nm and has to be adjusted according to the dimension of the biological entity that's being embedded into the aperture. For a given protein biosensor the corresponding solid-state aperture is usually smaller than the diameter of the protein biosensor ensuring efficient embedment. Alternatively, the orifice of the solid-state nanohole may be drilled at a larger diameter than the protein biosensor and subsequently reduced by means of shrinking the initial hole (Li, J. et al. Ion-beam sculpting at nanometer length scales. Nature 412, 166-169 (2001).

In a preferred embodiment a helium ion microscope may be used to drill the synthetic nanopores. A chip that supports one or more regions of a thin-film material that has been processed to be a free-standing membrane is introduced to the helium ion microscope (HIM) chamber. HIM motor controls are used to bring a free-standing membrane into the path of the ion beam while the microscope is set for low magnification. Beam parameters including focus and stigmation are adjusted at a region adjacent to the free-standing membrane, but on the solid substrate. Once the parameters have been properly fixed, the chip position is moved such that the free-standing membrane region is centered on the ion beam scan region and the beam is blanked. The HIM field of view is set to a dimension (in μm) that is sufficient to contain the entire anticipated nanopore pattern and sufficient to be useful in future optical readout (i.e. dependent on optical magnification, camera resolution, etc.). The ion beam is then rastered once through the entire field of view at a pixel dwell time that results in a total ion dose sufficient to remove all or most of the membrane autofluorescence. The field of view is then set to the proper value (smaller than that used above) to perform lithographically-defined milling of either a single nanopore or an array of nanopores. The pixel dwell time of the pattern is set to result in nanopores of one or more predetermined diameters, determined through the use of a calibration sample prior to sample processing. This entire process is repeated for each desired region on a single chip and/or for each chip introduced into the HIM chamber.

In a preferred embodiment the solid-state substrate may be modified to generate active sites on the surface that allow the covalent attachment of the plugged in protein biosensor or to modify the surface properties in a way to make it more suitable for a given application. Such modifications may be of covalent or non-covalent nature. A covalent surface modification includes a silanization step where an organosilane compound binds to silanol groups on the solid surface. For instance, the alkoxy groups of an alkoxysilane are hydrolyzed to form silanol-containing species. Reaction of these silanes involves four steps. Initially, hydrolysis of the labile groups occurs. Condensation to oligomers follows. The oligomers then hydrogen bond with hydroxyl groups of the substrate. Finally, during drying or curing, a covalent linkage is formed with the substrate with concomitant loss of water. For covalent attachment organosilanes with active side groups may be employed. Such side groups consist of, but are not limited to epoxy side chain, aldehydes, isocyanates, isothiocyanates, azides or alkynes (click chemistry) to name a few. For someone skilled in the art it is obvious that multiple ways of covalently attaching a protein to a surface are possible. For instance, certain side groups on an organosilane may need to be activated before being capable of binding a protein (e.g. primary amines or carboxyl side groups activated with an N-hydroxysuccinimidester). Another way of attaching a protein to the solid surface may be achieved through affinity binding by having one affinity partner attached to the protein and the second affinity partner being located on the solid surface. Such affinity pairs consist of the group of, but are not limited to biotin-strepavidin, antigen-antibody and aptamers and the corresponding target molecules. In a preferred embodiment the surface modification of the solid state nanopore includes treatment with an organosilane that renders the surface hydrophobic. Such organosilanes include but are not limited to, alkanesilanes (e.g. octadecyldimethylchlorosilane) or modified alkanesilanes such as fluorinated alkanesilanes with an alkane chain length of 5 to 30 carbons. The hydrophobic surface is then treated with a dilute solution of a lipid in pentane. After drying of the solvent and immersing the surface in an aqueous solution the lipid will spontaneously form a layer on the surface. A layer of lipid on the solid surface might proof beneficial for the formation of a hybrid nanopore. The lipid layer on the solid phase might reduce the leak current between protein and solid state nanopore and it might increase the stability of the inserted protein pore. Combining a low capacitance solid substrate as well as a lipid coating of said substrate may render the hybrid nanopore system amenable to an electrical readout based on current fluctuations generated by translocation of DNA through the hybrid nanopore. To achieve electrical read out with such a system a means of decreasing the translocation speed of unmodified DNA must be combined with a lipid coated hybrid nanopore. Molecular motors such as polymerases or helicases may be combined with a hybrid nanopore and effectively reduce the translocation speed of DNA through the hybrid nanopore. The lipids used for coating the surface are from the group of sphingolipids, phospholipids or sterols. A method and/or system for sequencing a biological polymer or molecule (e.g., a nucleic acid) may include exciting one or more donor labels attached to a pore or nanopore. A biological polymer may be translocated through the pore or nanopore, where a monomer of the biological polymer is labeled with one or more acceptor labels. Energy may be transferred from the excited donor label to the acceptor label of the monomer as, after or before the labeled monomer passes through, exits or enters the pore or nanopore. Energy emitted by the acceptor label as a result of the energy transfer may be detected, where the energy emitted by the acceptor label may correspond to or be associated with a single or particular monomer (e.g., a nucleotide) of a biological polymer. The sequence of the biological polymer may then be deduced or sequenced based on the detection of the emitted energy from the monomer acceptor label which allows for the identification of the labeled monomer. A pore, nanopore, channel or passage, e.g., an ion permeable pore, nanopore, channel or passage may be utilized in the systems and methods described herein.

Nanopore energy transfer sequencing (NETS) can be used to sequence nucleic acid. NETS can enable the sequencing of whole genomes within days for a fraction of today's cost which will revolutionize the understanding, diagnosis, monitoring and treatment of disease. The system or method can utilize a pore or nanopore (synthetic or protein-based) of which one side, either the cis (−) or trans (+) side of the pore is labeled with one or multiple or a combination of different energy absorbers or donor labels, such as fluorophores, fluorescent proteins, quantum dots, metal nanoparticles, nanodiamonds, etc. Multiple labels and methods of labeling a nanopore are described in U.S. Pat. No. 6,528,258, the entirety of which is incorporated herein by reference.

A nucleic acid can be threaded through a nanopore by applying an electric field through the nanopore (Kasianowicz, J. J. et al., Characterization of individual polynucleotide molecules using a membrane channel. Proc. Natl. Acad. Sci USA 93 (1996): 13770-13773). A nucleic acid to be translocated through the nanopore may undergo a labeling reaction where naturally occurring nucleotides are exchanged with a labeled, energy emitting or absorbing counterpart or modified counterparts that can be subsequently modified with an energy emitting or absorbing label, i.e., an acceptor label. The labeled nucleic acid may then be translocated through the nanopore and upon entering, exiting or while passing through the nanopore a labeled nucleotide comes in close proximity to the nanopore or donor label. For example, within 1-10 nm or 1-2 nm of the nanopore donor label. The donor labels may be continuously illuminated with radiation of appropriate wavelength to excite the donor labels. Via a dipole-dipole energy exchange mechanism called FRET (Stryer, L. Annu Rev Biochem. 47 (1978): 819-846), the excited donor labels transfer energy to a bypassing nucleic acid or acceptor label. The excited acceptor label may then emit radiation, e.g., at a lower energy than the radiation that was used to excite the donor label. This energy transfer mechanism allows the excitation radiation to be "focused" to interact with the acceptor labels with sufficient resolution to generate a signal at the single nucleotide scale.

A nanopore may include any opening positioned in a substrate that allows the passage of a molecule through the substrate. For example, the nanopore may allow passage of a molecule that would otherwise not be able to pass through that substrate. Examples of nanopores include proteinaceous or protein based pores or synthetic pores. A nanopore may have an inner diameter of 1-10 nm or 1-5 nm or 1-3 nm.

Examples of protein pores include but are not limited to, alpha-hemolysin, voltage-dependent mitochondrial porin (VDAC), OmpF, OmpC, MspA and LamB (maltoporin) (Rhee, M. et al., Trends in Biotechnology, 25(4) (2007): 174-181). Any protein pore that allows the translocation of single nucleic acid molecules may be employed. A pore protein may be labeled at a specific site on the exterior of the pore, or at a specific site on the exterior of one or more monomer units making up the pore forming protein.

A synthetic pore may be created in various forms of solid substrates, examples of which include but are not limited to silicones (e.g. Si3N4, SiO2), metals, metal oxides (e.g. Al2O3) plastics, glass, semiconductor material, and combinations thereof. A synthetic nanopore may be more stable than a biological protein pore positioned in a lipid bilayer membrane.

Synthetic nanopores may be created using a variety of methods. For example, synthetic nanopores may be created by ion beam sculpting (Li, J. et al., Nature 412 (2001): 166-169) where massive ions with energies of several thousand electron volts (eV) cause an erosion process when fired at a surface which eventually will lead to the formation of a nanopore. A synthetic nanopore may be created via latent track etching. For example, a single conical synthetic nanopore may be created in a polymer substrate by chemically etching the latent track of a single, energetic heavy ion. Each ion produces an etchable track in a polymer foil, forming a one-pore membrane (Heins, E. A. et al., Nano Letters 5 (2005): 1824-1829). A synthetic nanopore may also be created by a method called Electron beam-induced fine tuning. Nanopores in various materials have been fabricated by advanced nanofabrication techniques, such as FIB drilling and electron (E) beam lithography, followed by E-beam assisted fine tuning techniques. With the appropriate electron beam intensity applied, a previously prepared nanopore will start to shrink. The change in pore diameter may be monitored in real-time using a TEM (transmission electron microscope), providing a feedback mechanism to switch off the electron beam at any desired dimension of the nanopore (Lo, C. J. et al., Nanotechnology 17 (2006): 3264-67).

A synthetic nanopore may also be created by using a carbon nanotube embedded in a suitable substrate such as but not limited to polymerized epoxy. Carbon nanotubes can have uniform and well-defined chemical and structural properties. Various sized carbon nanotubes can be obtained, ranging from one to hundreds of nanometers. The surface charge of a carbon nanotube is known to be about zero, and as a result, electrophoretic transport of a nucleic acid through the nanopore becomes simple and predictable (Ito, T. et al., Chem. Commun. 12 (2003): 1482-83).

The substrate surface of a synthetic nanopore may be chemically modified to allow for covalent attachment of the protein pore or to render the surface properties suitable for optical nanopore sequencing. Such surface modifications can be covalent or non-covalent. Most covalent modification include an organosilane deposition for which the most common protocols are described: 1) Deposition from aqueous alcohol. This is the most facile method for preparing silylated surfaces. A 95% ethanol-5% water solution is adjusted to pH 4.5-5.5 with acetic acid. Silane is added with stirring to yield a 2% final concentration. After hydrolysis and silanol group formation the substrate is added for 2-5 min. After rinsed free of excess materials by dipping briefly in ethanol. Cure of the silane layer is for 5-10 min at 110 degrees Celsius. 2) Vapor Phase Deposition. Silanes can be applied to substrates under dry aprotic conditions by chemical vapor deposition methods. These methods favor monolayer deposition. In closed chamber designs, substrates are heated to sufficient temperature to achieve 5 mm vapor pressure. Alternatively, vacuum can be applied until silane evaporation is observed. 3) Spin-on deposition. Spin-on applications can be made under hydrolytic conditions which favor maximum functionalization and polylayer deposition or dry conditions which favor monolayer deposition.

A pore may have two sides. One side is referred to as the "cis" side and faces the (−) negative electrode or a negatively charged buffer/ion compartment or solution. The other side is referred to as the "trans" side and faces the (+) electrode or a positively charged buffer/ion compartment or solution. A biological polymer, such as a labeled nucleic acid molecule or polymer can be pulled or driven through the pore by an electric field applied through the nanopore, e.g., entering on the cis side of the nanopore and exiting on the trans side of the nanopore.

The nanopore may have one or more labels attached. In a preferred embodiment the label is a member of a Forster Resonance Energy Transfer (FRET) pair. The label consist of the group of organic fluorophores, chemiluminescent labels, quantum dots, metallic nanoparticles and fluorescent proteins. The nucleic acid may have one distinct label per nucleotide. The labels attached to the nucleotides consist of the group of organic fluorophores, chemiluminescent labels, quantum dots, metallic nanoparticles and fluorescent proteins. The label attachment site in the pore protein can be generated by protein engineering e.g. a mutant protein can be constructed that will allow the specific binding of the label. As an example, a cysteine residue may be inserted at the desired position of the protein which inserts a thiol (SH) group that can be used to attach a label. The cysteine can either replace a natural occurring amino acid or can be incorporated as an addition amino acid. Care must be taken not to disrupt the biological function of the protein. A malemeide-activated label is then covalently attached to the thiol residue of the protein nanopore. In a preferred embodiment the attachment of the label to the protein nanopore or the label on the nucleic acid is reversible. By implementing a cleavable crosslinker, an easily breakable chemical bond (e.g. an S—S bond or a pH labile bond) is introduced and the label may be removed when the corresponding conditions are met.

A nanopore or pore may be labeled with one or more donor labels. For example, the cis side or surface and/or trans side or surface of the nanopore may be labeled with one or more donor labels. The label may be attached to the base of a pore or nanopore or to another portion or monomer making up the nanopore or pore A label may be attached to a portion of the membrane or substrate through which a nanopore spans or to a linker or other molecule attached to the membrane, substrate or nanopore. The nanopore or pore label may be positioned or attached on the nanopore, substrate or membrane such that the pore label can come into proximity with an acceptor label of a biological polymer, e.g., a nucleic acid, which is translocated through the pore. The donor labels may have the same or different emission or absorption spectra.

The labeling of a pore structure may be achieved via covalent or non-covalent interactions. Examples of such interactions include but are not limited to interactions based on hydrogen bonds, hydrophobic interactions, electrostatic interactions, ionic interactions, magnetic interactions, Van der Walls forces or combinations thereof.

A donor label may be placed as close as possible to the aperture of a nanopore without causing an occlusion that impairs translocation of a nucleic acid through the nanopore (see e.g., FIGS. 1A-1D). A pore label may have a variety of suitable properties and/or characteristics. For example, a pore label may have energy absorption properties meeting particular requirements. A pore label may have a large radiation energy absorption cross-section, ranging, for example, from about 0 to 1000 nm or from about 200 to 500 nm. A pore label may absorb radiation within a specific energy range that is higher than the energy absorption of the nucleic acid label. The absorption energy of the pore label may be tuned with respect to the absorption energy of a nucleic acid label in order to control the distance at which energy transfer may occur between the two labels. A pore label may be stable and functional for at least $10^6$ or $10^9$ excitation and energy transfer cycles.

Pore proteins are chosen from a group of proteins such as, but not limited to, alpha-hemolysin, MspA, voltage-dependent mitochondrial porin (VDAC), Anthrax porin, OmpF, OmpC and LamB (maltoporin). Integration of the pore protein into the solid state hole is accomplished by attaching a charged polymer to the pore protein. After applying an electric field the charged complex is electrophoretically pulled into the solid state hole.

Nanopore Labels

A pore label may include one or more Quantum dots. A Quantum dot has been demonstrated to have many or all of the above described properties and characteristics found in suitable pore labels (Bawendi M. G. in U.S. Pat. No. 6,251,303). Quantum Dots are nanometer scale semiconductor crystals that exhibit strong quantum confinement due to the crystals radius being smaller than the Bohr exciton radius. Due to the effects of quantum confinement, the bandgap of the quantum dots increases with decreasing crystal size thus allowing the optical properties to be tuned by controlling the crystal size (Bawendi M. G. et al., in U.S. Pat. No. 7,235,361 and Bawendi M. G. et al., in U.S. Pat. No. 6,855,551).

One example of a Quantum dot which may be utilized as a pore label is a CdTe quantum dot which can be synthesized in an aqueous solution. A CdTe quantum dot may be functionalized with a nucleophilic group such as primary amines, thiols or functional groups such as carboxylic acids. A CdTe quantum dot may include a mercaptopropionic acid capping ligand, which has a carboxylic acid functional group that may be utilized to covalently link a quantum dot to a primary amine on the exterior of a protein pore. The cross-linking reaction may be accomplished using standard cross-linking reagents (homo-bifunctional as well as hetero-bifunctional) which are known to those having ordinary skill in the art of bioconjugation. Care may be taken to ensure that the modifications do not impair or substantially impair the translocation of a nucleic acid through the nanopore. This may be achieved by varying the length of the employed crosslinker molecule used to attach the donor label to the nanopore.

The primary amine of the Lysin residue 131 of the natural alpha hemolysin protein (Song, L. et al., Science 274, (1996): 1859-1866) may be used to covalently bind carboxy modified CdTe Quantum dots via 1-Ethyl-3-[3-dimethylaminopropyl]carbodiimide hydrochloride/N-hydroxysulfosuccinimide (EDC/NHS) coupling chemistry. Alternatively, amino acid 129 (threonine) may be exchanged into cysteine. Since there is no other cysteine residue in the natural alpha hemolysin protein the thiol side group of the newly inserted cysteine may be used to covalently attach other chemical moieties.

A variety of methods, mechanisms and/or routes for attaching one or more pore labels to a pore protein may be utilized. A pore protein may be genetically engineered in a manner that introduces amino acids with known properties or various functional groups to the natural protein sequence. Such a modification of a naturally occurring protein sequence may be advantageous for the bioconjugation of Quantum dots to the pore protein. For example, the introduction of a cysteine residue would introduce a thiol group that would allow for the direct binding of a Quantum dot, such as a CdTe quantum dot, to a pore protein. Also, the introduction of a Lysin residue would introduce a primary amine for binding a Quantum dot. The introduction of glutamic acid or aspartic acid would introduce a carboxylic acid moiety for binding a Quantum dot. These groups are amenable for bioconjugation with a Quantum dot using either homo- or hetero-bifunctional crosslinker molecules. Such modifications to pore proteins aimed at the introduction of functional groups for bioconjugation are known to those having ordinary skill in the art. Care should be taken to ensure that the modifications do not impair or substantially impair the translocation of a nucleic acid through the nanopore.

The nanopore label can be attached to a protein nanopore before or after insertion of said nanopore into a lipid bilayer. Where a label is attached before insertion into a lipid bilayer, care may be taken to label the base of the nanopore and avoid random labeling of the pore protein. This can be achieved by genetic engineering of the pore protein to allow site specific attachment of the pore label (see section 0047). An advantage of this approach is the bulk production of labeled nanopores. Alternatively, a labeling reaction of a pre-inserted nanopore may ensure site-specific attachment of the label to the base (trans-side) of the nanopore without genetically engineering the pore protein.

A biological polymer, e.g., a nucleic acid molecule or polymer, may be labeled with one or more acceptor labels. For a nucleic acid molecule, each of the four nucleotides or building blocks of a nucleic acid molecule may be labeled with an acceptor label thereby creating a labeled (e.g., fluorescent) counterpart to each naturally occurring nucleotide. The acceptor label may be in the form of an energy accepting molecule which can be attached to one or more nucleotides on a portion or on the entire strand of a converted nucleic acid.

A variety of methods may be utilized to label the monomers or nucleotides of a nucleic acid molecule or polymer. A labeled nucleotide may be incorporated into a nucleic acid during synthesis of a new nucleic acid using the original sample as a template ("labeling by synthesis"). For example, the labeling of nucleic acid may be achieved via PCR, whole genome amplification, rolling circle amplification, primer extension or the like or via various combinations and extensions of the above methods known to persons having ordinary skill in the art.

Labeling of a nucleic acid may be achieved by replicating the nucleic acid in the presence of a modified nucleotide analog having a label, which leads to the incorporation of that label into the newly generated nucleic acid. The labeling process can also be achieved by incorporating a nucleotide analog with a functional group that can be used to covalently attach an energy accepting moiety in a secondary labeling step. Such replication can be accomplished by whole genome amplification (Zhang, L. et al., Proc. Natl. Acad. Sci. USA 89 (1992): 5847) or strand displacement amplification such as rolling circle amplification, nick translation, transcription, reverse transcription, primer extension and polymerase chain reaction (PCR), degenerate oligonucleotide primer PCR (DOP-PCR) (Telenius, H. et al., Genomics 13 (1992): 718-725) or combinations of the above methods.

A label may comprise a reactive group such as a nucleophile (amines, thiols etc.). Such nucleophiles, which are not present in natural nucleic acids, can then be used to attach fluorescent labels via amine or thiol reactive chemistry such as NHS esters, maleimides, epoxy rings, isocyanates etc. Such nucleophile reactive fluorescent dyes (i.e. NHS-dyes) are readily commercially available from different sources. An advantage of labeling a nucleic acid with small nucleophiles lies in the high efficiency of incorporation of such labeled nucleotides when a "labeling by synthesis" approach is used. Bulky fluorescently labeled nucleic acid building blocks may be poorly incorporated by polymerases due to steric hindrance of the labels during the polymerization process into newly synthesized DNA.

DNA can be directly chemically modified without polymerase mediated incorporation of labeled nucleotides. One example of a modification includes cis-platinum containing dyes that modify Guanine bases at their N7 position (Hoevel, T. et al., Bio Techniques 27 (1999): 1064-1067). Another example includes the modifying of pyrimidines with hydroxylamine at the C6 position which leads to 6-hydroxylamino derivatives. The resulting amine groups can be further modified with amine reactive dyes (e.g. NHS-Cy5).

A nucleic acid molecule may be directly modified with N-Bromosuccinimide which upon reacting with the nucleic acid will result in 5-Bromocystein, 8-Bromoadenine and 8-Bromoguanine. The modified nucleotides can be further reacted with di-amine nucleophiles. The remaining nucleophile can then be reacted with an amine reactive dye (e.g. NHS-dye) (Hermanson G. in Bioconjugate Techniques, Academic Press 1996, ISBN 978-0-12-342336-8).

A combination of 1, 2, 3 or 4 nucleotides in a nucleic acid strand may be exchanged with their labeled counterpart. The various combinations of labeled nucleotides can be sequenced in parallel, e.g., labeling a source nucleic acid or DNA with combinations of 2 labeled nucleotides in addition to the four single labeled samples, which will result in a total of 10 differently labeled sample nucleic acid molecules or DNAs (G, A, T, C, GA, GT, GC, AT, AC, TC). The resulting sequence pattern may allow for a more accurate sequence alignment due to overlapping nucleotide positions in the redundant sequence read-out.

A method for sequencing a polymer, such as a nucleic acid molecule includes providing a nanopore or pore protein (or a synthetic pore) inserted in a membrane or membrane like structure or other substrate. The base or other portion of the pore may be modified with one or more pore labels. The base may refer to the Trans side of the pore. Optionally, the Cis and/or Trans side of the pore may be modified with one or more pore labels. Nucleic acid polymers to be analyzed or sequenced may be used as a template for producing a labeled version of the nucleic acid polymer, in which one of the four nucleotides or up to all four nucleotides in the resulting polymer is/are replaced with the nucleotide's labeled analogue(s). An electric field is applied to the nanopore which forces the labeled nucleic acid polymer through the nanopore, while an external monochromatic or other light source may be used to illuminate the nanopore, thereby exciting the pore label. As, after or before labeled nucleotides of the nucleic acid pass through, exit or enter the nanopore, energy is transferred from the pore label to a nucleotide label, which results in emission of lower energy radiation. The nucleotide label radiation is then detected by a confocal microscope setup or other optical detection system or light microscopy system capable of single molecule detection known to people having ordinary skill in the art. Examples of such detection systems include but are not limited to confocal microscopy, epifluorescent microscopy and total internal reflection fluorescent (TIRF) microscopy. Other polymers (e.g., proteins and polymers other than nucleic acids) having labeled monomers may also be sequenced according to the methods described herein.

Energy may be transferred from a pore or nanopore donor label (e.g., a Quantum Dot) to an acceptor label on a polymer (e.g., a nucleic acid) when an acceptor label of an acceptor labeled monomer (e.g., nucleotide) of the polymer interacts with the donor label as, after or before the labeled monomer exits, enters or passes through a nanopore. For example, the donor label may be positioned on or attached to the nanopore on the cis or trans side or surface of the nanopore such that the interaction or energy transfer between the donor label and acceptor label does not take place until the labeled monomer exits the nanopore and comes into the vicinity or proximity of the donor label outside of the nanopore channel or opening. As a result, interaction between the labels, energy transfer from the donor label to the acceptor label, emission of energy from the acceptor label and/or measurement or detection of an emission of energy from the acceptor label may take place outside of the passage, channel or opening running through the nanopore, e.g., within a cis or trans chamber on the cis or trans sides of a nanopore. The measurement or detection of the energy emitted from the acceptor label of a monomer may be utilized to identify the monomer.

The nanopore label may be positioned outside of the passage, channel or opening of the nanopore such that the label may be visible or exposed to facilitate excitation or illumination of the label. The interaction and energy transfer between a donor label and accepter label and the emission of energy from the acceptor label as a result of the energy transfer may take place outside of the passage, channel or opening of the nanopore. This may facilitate ease and accuracy of the detection or measurement of energy or light emission from the acceptor label, e.g., via an optical detection or measurement device. The donor and acceptor label interaction may take place within a channel of a nanopore and a donor label could be positioned within the channel of a nanopore.

A donor label may be attached in various manners and/or at various sites on a nanopore. For example, a donor label may be directly or indirectly attached or connected to a portion or unit of the nanopore. Alternatively, a donor label may be positioned adjacent to a nanopore.

Each acceptor labeled monomer (e.g., nucleotide) of a polymer (e.g., nucleic acid) can interact sequentially with a donor label positioned on or next to or attached directly or indirectly to a nanopore or channel through which the polymer is translocated. The interaction between the donor and acceptor labels may take place outside of the nanopore channel or opening, e.g., after the acceptor labeled monomer exits the nanopore or before the monomer enters the nanopore. The interaction may take place within or partially within the nanopore channel or opening, e.g., while the acceptor labeled monomer passes through, enters or exits the nanopore.

When one of the four nucleotides of a nucleic acid is labeled, the time dependent signal arising from the single nucleotide label emission is converted into a sequence corresponding to the positions of the labeled nucleotide in the nucleic acid sequence. The process is then repeated for each of the four nucleotides in separate samples and the four partial sequences are then aligned to assemble an entire nucleic acid sequence.

When multi-color labeled nucleic acid (DNA) sequences are analyzed, the energy transfer from one or more donor labels to each of the four distinct acceptor labels that may exist on a nucleic acid molecule may result in light emission at four distinct wavelengths or colors (each associated with one of the four nucleotides) which allows for a direct sequence read-out.

Unmodified DNA translocation through a nanopore occurs with a frequency of $10^5$-$10^6$ nucleotides per second. Therefore, a direct sequence read out becomes challenging mainly due to the limited bandwidth of the recording equipment. Different strategies have been employed to slow down the translocation speed of nucleic acid through a nanopore. The most popular approach involves the combination of a nanopore with a molecular motor that actively pulls or pushes the nucleic acid through the nanopore. These enzymatic motor proteins usually operate at a frequency of 10-50 nucleotides per second, sufficiently slow to allow single nucleotide discrimination in a nanopore. Other ways of slowing down the DNA translocation rate are described in the literature and include different ways of increasing the viscosity of the translocation medium; however those approaches also reduced the conductance of the nanopore which abolishes the nucleotide discrimination capabilities.

Another approach to reduce the translocation speed of DNA through a nanopore is described in provisional application 61/648,249 (Nanopore sequencing using current modulators) which is hereby incorporate in its entirety. By incorporating modified nucleotides into a DNA strand said DNA strands nominal diameter is increased which results in a higher friction when translocating through a nanopore. The higher friction results in a reduced translocation speed. Such modified nucleotides may constitute, but not limited to fluorescent labeled nucleotides. The fluorescent labels do not only slow down the DNA translocation but also allow the optical detection in optical nanopore sequencing approaches. For an optical detection the preferred translocation rate of nucleic acid through a nanopore ranges from 1-1000 nucleotides per second.

Translocation Speed

A major obstacle associated with Nanopore based sequencing approaches is the high translocation velocity of nucleic acid through a nanopore (~500.000-1.000.000 nucleotides/sec) which doesn't allow for direct sequence readout due to the limited bandwidth of the recording equipment. A way of slowing down the nucleic acid translocation with two different nanopore proteins was recently shown by Cherf et al. (Nat Biotechnol. 2012 Feb. 14; 30(4):344-8) and Manrao et al. (Nat Biotechnol. 2012 Mar. 25; 30(4):349-53) and are incorporated herein by reference. Both groups used a DNA polymerase to synthesize a complementary strand from a target template which resulted in the step-wise translocation of the template DNA through the nanopore. Hence, the synthesis speed of the nucleic acid polymerase (10-500 nucleotides/sec) determined the translocation speed of the DNA and since it's roughly 3-4 orders of magnitude slower than direct nucleic acid translocation the analysis of single nucleotides became feasible. However, the polymerase-aided translocation requires significant sample preparation to generate a binding site for the polymerase and the nucleic acid synthesis has to be blocked in bulk and can only start once the nucleic acid-polymerase complex is captured by the nanopore protein. This results in a rather complex set-up which might prevent the implementation in a commercial setting. Furthermore, fluctuation in polymerase synthesis reactions such as a stalled polymerization as well as the dissociation of the polymerase from the nucleic acid may hamper the sequence read-out resulting in a high error rate and reduced read-length, respectively. Optical Nanopore sequence as described in this application uses a different way of slowing down the DNA translocation. A target nucleic acid is enzymatically copied by incorporating fluorescent modified nucleotides. The resulting labeled nucleic acid has an increased nominal diameter which results in a decreased translocation velocity when pulled through a nanopore. The preferred translocation rate for optical sequencing lies in the range of 1-1000 nucleotides per second with a more preferred range of 200-800 nucleotides per second and a most preferred translocation rate of 200-600 nucleotides per second.

Signal Detection

During sequencing of a nucleic acid molecule, the energy transfer signal may be generated with sufficient intensity that a sensitive detection system can accumulate sufficient signal within the transit time of a single nucleotide through the nanopore to distinguish a labeled nucleotide from an unlabeled nucleotide. Therefore, the pore label may be stable, have a high absorption cross-section, a short excited state lifetime, and/or temporally homogeneous excitation and energy transfer properties. The nucleotide label may be capable of emitting and absorbing sufficient radiation to be detected during the transit time of the nucleotide through the pore. The product of the energy transfer cross-section, emission rate, and quantum yield of emission may yield sufficient radiation intensity for detection within the single nucleotide transit time. A nucleotide label may also be sufficiently stable to emit the required radiation intensity and without transience in radiation emission.

The excitation radiation source may be of high enough intensity that when focused to the diffraction limit on the nanopore, the radiation flux is sufficient to saturate the pore label. The detection system may filter out excitation radiation and pore label emission while capturing nucleic acid label emission during pore transit with sufficient signal-to-noise ratio (S/N) to distinguish a labeled nucleotide from an unlabeled nucleotide with high certainty. The collected nucleic acid label radiation may be counted over an integration time equivalent to the single nucleotide pore transit time.

A software signal analysis algorithm may then be utilized which converts the binned radiation intensity signal to a sequence corresponding to a particular nucleotide. Combination and alignment of four individual nucleotide sequences (where one of the four nucleotides in each sequence is labeled) allows construction of the complete nucleic acid sequence via a specifically designed computer algorithm.

A system for sequencing one or more biological polymers, e.g., nucleic acid molecules, may include a fixture or pore holder. The pore holder may include a hybrid nanopore assembly wherein one or more nanopores span a solid state membrane. The hybrid nanopore assembly has a Cis (−) side and a Trans (+) side. One or more labels may be attached to the nanopores. Alternatively, a label may be attached to a portion of the substrate through which the nanopore spans or to a linker or other molecule attached to the membrane, substrate or nanopore. An aqueous buffer solution is provided which surrounds the nanopore membrane assembly. The pore holder may contain two electrodes. A negative electrode or terminal may be positioned on the Cis side of the nanopore membrane assembly and a positive electrode or terminal may be positioned on the Trans side of the nanopore membrane assembly.

A flow of fluid or solution is provided on the side of the nanopore where the translocated polymer or nucleic acid exits after translocation through the nanopore. The flow may be continuous or constant such that the fluid or solution does not remain static for an extended period of time. The fluid flow or motion helps move or transfer translocated polymers away from the nanopore channel such the translocated polymers do not linger or accumulated near the nanopore channel exit or opening and cause fluorescent background or noise which could disrupt or prevent an accurate reading, measurement or detection of the energy emitted by a polymer acceptor label. Translocated polymers may include labels that were not fully exhausted, i.e. haven't reached their fluorescent lifetime and are still able to emit light. Such labels could interfere with the energy transfer between donor labels and subsequent monomer labels or emit energy that may interfere with the emission from other labels and disrupt an accurate reading or detection of energy from a labeled monomer.

One or more polymers, e.g., nucleic acid polymers or molecules, to be analyzed may also be provided. A polymer or nucleic acid polymer or molecule may include one or more labels, e.g., one or more monomers or nucleotides of the polymer may be labeled. A nucleic acid molecule may be loaded into a port positioned on the Cis side of then nanopore membrane assembly. The membrane segregates the nucleic acids to be analyzed to the Cis side of the nanopore membrane assembly. An energy source for exciting the nanopore label is provided, e.g., an illumination source. An electric field may be applied to or by the electrodes to force the labeled nucleic acid to translocate through the nanopore into the Cis side and out of the Trans side of the nanopore, from the Cis to the Trans side of the membrane, e.g., in a single file (Kasianowicz, J. J. et al., Proc. Natl. Acad. Sci USA 93 (1996): 13770-13773). Optionally, an electrical field may be applied utilizing other mechanisms to force the labeled nucleic acid to translocate through the nanopore. When a nucleic acid molecule is translocated through the nanopore and a labeled nucleotide comes into close proximity with the nanopore label, e.g., upon or after exiting the nanopore, energy is transferred from the excited nanopore label to a nucleotide label. A detector or detection system, e.g., optical detection system, for detecting or measuring energy emitted from the nucleotide label as a result of the transfer of energy from the nanopore label to the nucleotide label may also be provided.

The pore may be labeled with one or more donor labels in the form of quantum dots, metal nanoparticles, nano diamonds or fluorophores. The pore may be illuminated by monochromatic laser radiation. The monochromatic laser radiation may be focused to a diffraction limited spot exciting the quantum dot pore labels. As the labeled nucleic acid (e.g., labeled with an acceptor label in the form of a fluorophore) is translocated through the nanopore, the pore donor label (also "pore label" or "donor label") and a nucleotide acceptor label come into close proximity with one another and participate in a FRET (Förster resonance energy transfer) energy exchange interaction between the pore donor label and nucleic acid acceptor label (Ha, T. et al., Proc. Natl. Acad. Sci USA 93 (1996): 6264-6268).

FRET is a non-radiative dipole-dipole energy transfer mechanism from a donor to acceptor fluorophore. The efficiency of FRET may be dependent upon the distance between donor and acceptor as well as the properties of the fluorophores (Stryer, L., Annu Rev Biochem. 47 (1978): 819-846).

A fluorophore may be any construct that is capable of absorbing light of a given energy and re-emitting that light at a different energy. Fluorophores include, e.g., organic molecules, rare-earth ions, metal nanoparticles, nanodiamonds and semiconductor quantum dots.

Figure 2A:
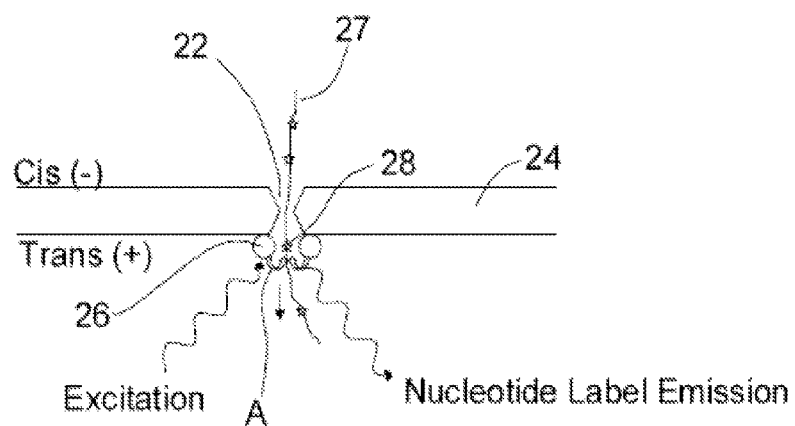
FIGS. 2A-2D illustrate one embodiment of a nanopore energy transfer sequencing method using hybrid nanopores.

FIG. 2A shows one variation of a FRET interaction between a pore donor label 26 on a synthetic nanopore 22 and a nucleic acid acceptor label 28 on a nucleic acid 27 (e.g., a single or double stranded nucleic acid), which is being translocated through the synthetic nanopore 22. The synthetic nanopore 22 is positioned in a substrate 24. FRET is a non-radiative dipole-dipole energy transfer mechanism from a donor label 26 to an acceptor label 28 (e.g., a fluorophore). The efficiency of the energy transfer is, among other variables, dependent on the physical distance between acceptor label 28 and the donor label.

The nucleic acid acceptor label 28 positioned on a nucleotide of the nucleic acid moves into close proximity with an excited nanopore donor label 26, e.g., as or after the label 28 or labeled nucleotide exits the nanopore 22, and gets excited via FRET (indicated by the arrow A showing energy transfer from the pore label 26 to the nucleic acid label 28). As a result, the nucleic acid label 28 emits light of a specific wavelength, which can then be detected with the appropriate optical equipment or detection system in order to identify the labeled nucleotide corresponding to or associated with the detected wavelength of emitted light.

Figure 2B:
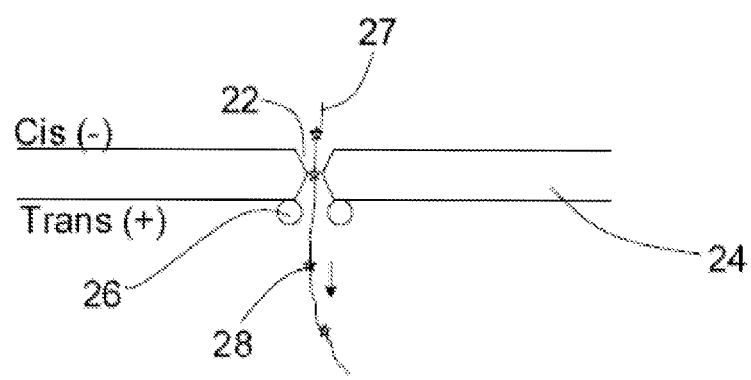

FIG. 2B shows translocation of the labeled nucleic acid 27 at a point in time where no FRET is taking place (due to the acceptor and donor labels not being in close enough proximity to each other). This is indicated by the lack of any arrows showing energy transfer between a pore label 26 and a nucleic acid label 28.

Figure 2C:
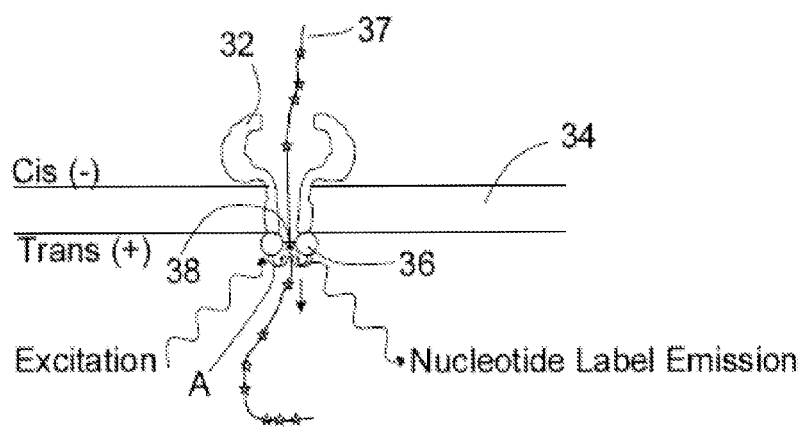

FIG. 2C shows one variation of a FRET interaction between a pore donor label 36 on a proteinaceous or protein nanopore 32 and a nucleic acid acceptor label 38 on a nucleic acid 37 (e.g., a single or double stranded nucleic acid), which is being translocated through the protein pore or nanopore 32. The pore protein 32 is positioned in a lipid bilayer 34. The nucleic acid acceptor label 38 positioned on a nucleotide of the nucleic acid moves into close proximity with an excited nanopore donor label 36, e.g., as or after the label 38 or labeled nucleotide exits the nanopore 32, and gets excited via FRET (indicated by the arrow A showing energy transfer from the pore label 36 to the nucleic acid label 38). As a result, the nucleic acid label 38 emits light of a specific wavelength, which can be detected with the appropriate optical equipment or detection system in order to identify the labeled nucleotide corresponding to or associated with the detected wavelength of emitted light.

Figure 2D:
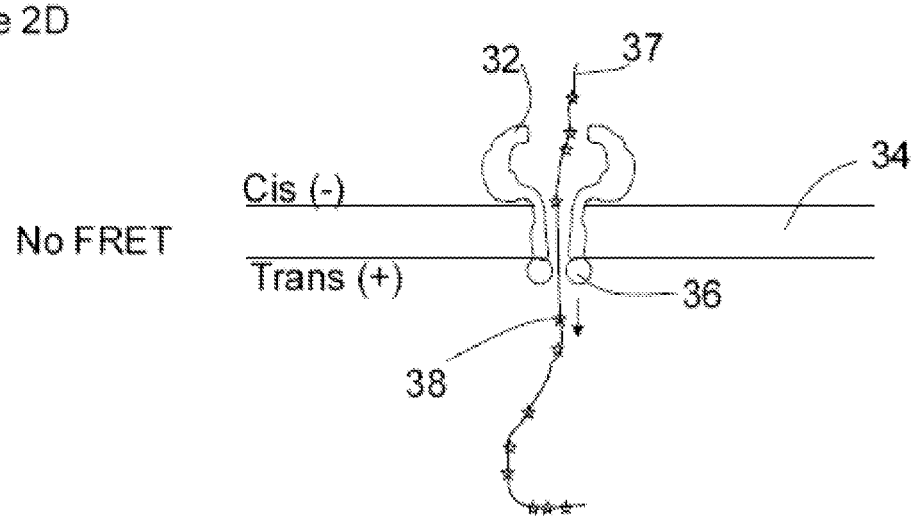

FIG. 2D shows translocation of the labeled nucleic acid 37 at a point in time where no FRET is taking place (due to the labels not being in close enough proximity to each other). This is indicated by the lack of arrows showing energy transfer between a pore donor label 36 and a nucleic acid label 38.

Three equations are also shown below: Equation (1) gives the Förster radius which is defined as the distance that energy transfer efficiency from donor to acceptor is 50%. The Förster distance depends on the refractive index ($n_D$), quantum yield of the donor ($Q_D$), spatial orientation (K) and the spectral overlap of the acceptor and donor spectrum (I). $N_A$ is the Avogadro number with $N_A=6.022\times10^{23}$ mol$^{-1}$ (see equation below). Equation (2) describes the overlap integral for the donor and acceptor emission and absorption spectra respectively; Equation (3) shows the FRET energy transfer efficiency as a function of distance between the acceptor and donor pair. The equations demonstrate that spectral overlap controls the Förster radius, which determines the energy transfer efficiency for a given distance between the FRET pair. Therefore by tuning the emission wavelength of the donor, the distance at which energy transfer occurs can be controlled.

$$R_0 = \left(\frac{9000(\ln 10)\kappa_P^2 Q_D}{N_A 128\pi^5 n_D^6}I\right)^{1/6} \quad (1)$$

$$I = \int J(\lambda)d\lambda = \int PL_{D-corr}(\lambda)\times\lambda^4\times\varepsilon_A(\lambda)d\lambda \quad (2)$$

$$E = \frac{k_{DA}}{k_{DA}+\tau_D^{-1}} = \frac{R_0^6}{R_0^6+r^6} \quad (3)$$

With respect to Quantum dots, due to the size dependent optical properties of quantum dots, the donor emission wavelength may be adjusted. This allows the spectral overlap between donor emission and acceptor absorption to be adjusted so that the Förster radius for the FRET pair may be controlled. The emission spectrum for Quantum dots is narrow, (e.g., 25 nm Full width-half maximum—FWHM—is typical for individual quantum dots) and the emission wavelength is adjustable by size, enabling control over the donor label-acceptor label interaction distance by changing the size of the quantum dots. Another important attribute of quantum dots is their broad absorption spectrum, which allows them to be excited at energies that do not directly excite the acceptor label. The properties allow quantum dots of the properly chosen size to be used to efficiently transfer energy with sufficient resolution to excite individual labeled nucleotides as, after or before the labeled nucleotides travel through a donor labeled pore.

Following a FRET energy transfer, the pore donor label may return to the electronic ground state and the nucleotide acceptor label can re-emit radiation at a lower energy. Where fluorophore labeled nucleotides are utilized, energy transferred from the fluorophore acceptor label results in emitted photons of the acceptor label. The emitted photons of the acceptor label may exhibit lower energy than the pore label emission. The detection system for fluorescent nucleotide labels may be designed to collect the maximum number of photons at the acceptor label emission wavelength while filtering out emission from a donor label (e.g., quantum dot donors) and laser excitation. The detection system counts photons from the labeled monomers as a function of time. Photon counts are binned into time intervals corresponding to the translocation time of, for instance, a monomer comprising a single nucleotide in a nucleic acid polymer crossing the nanopore. Spikes in photon counts correspond to labeled nucleotides translocating across the pore. To sequence the nucleic acid, sequence information for a given nucleotide is determined by the pattern of spikes in photon counts as a function of time. An increase in photon counts is interpreted as a labeled nucleotide.

Translocation of nucleic acid polymers through the nanopore may be monitored by current measurements arising from the flow of ions through the nanopore. Translocating nucleic acids partially block the ionic flux through the pore resulting in a measurable drop in current. Thus, detection of a current drop represents detection of a nucleic acid entering the pore, and recovery of the current to the original value represents detection of a nucleic acid exiting the pore.

Figure 3A:
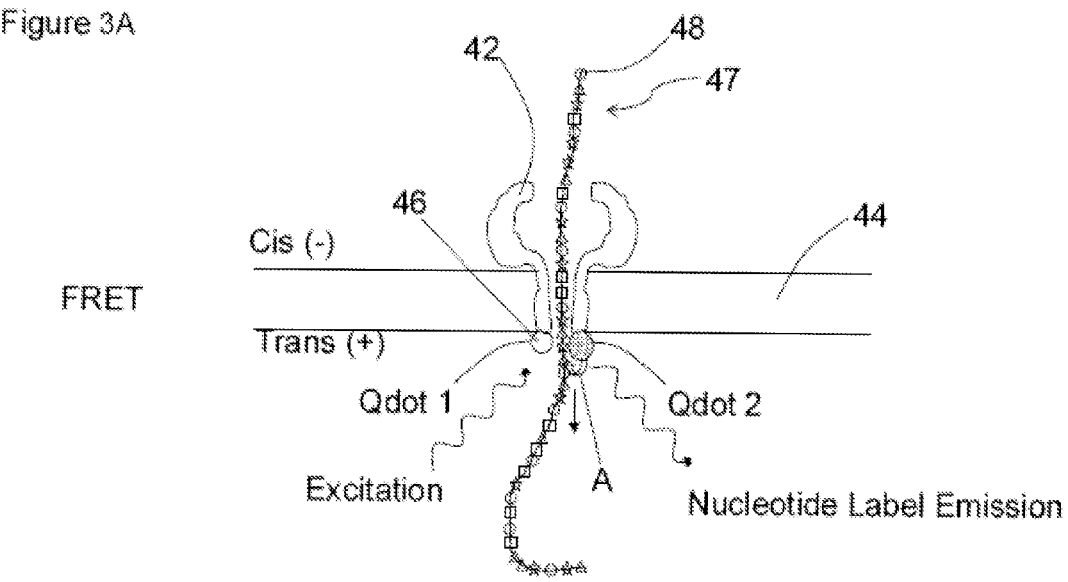
FIG. 3A illustrates one variation of a multicolor FRET interaction between the donor labels (Quantum dots) of a protein nanopore and the acceptor labels of a nucleic acid. Each shape on the nucleic acid represents a specific acceptor label, where each label has a distinct emission spectra associated with a specific nucleotide such that each label emits light at a specific wavelength associated with a specific nucleotide.

As mentioned supra, a multicolor FRET interaction is utilized to sequence a molecule such a nucleic acid. FIG. 3A shows one variation of a multicolor FRET interaction between one or more donor labels 46 (e.g., Quantum dots) of a protein nanopore 42 (lipid layer not shown) and one or more acceptor labels 48 of a nucleic acid molecule 47 (e.g., a single or double stranded nucleic acid). Each shape on the nucleic acid 47 represents a specific type of acceptor label labeling a nucleotide, where each label has a distinct emission spectra associated with or corresponding to a specific nucleotide such that each label emits light at a specific wavelength or color associated with a specific nucleotide.

In FIG. 3A, each of the four shapes (triangle, rectangle, star, circle) represents a specific acceptor label 48, each label having a distinct emission spectra (e.g., 4 different emission spectra). Each of the acceptor labels 48 can form a FRET pair with a corresponding donor label or quantum dot 46 attached to the base of the nanopore. Qdot1 and Qdot2 represent two different Quantum dots as donor labels 46 that form specific FRET pairs with a nucleic acid acceptor label 48. The Quantum dot donor labels 46 are in an excited state and depending on the particular acceptor label 48 that comes in proximity to the Quantum dots during, after or before a labeled nucleotide translocation through the nanopore 42, an energy transfer (arrow A) from the donor label 46 to the nucleotide acceptor label 48 takes place, resulting in a nucleotide label 48 energy emission. As a result, each nucleotide may emit light at a specific wavelength or color (due to the distinct emission spectrum of the nucleotide's label), which can be detected (e.g., by optical detection) and used to identify or deduce the nucleotide sequence of the nucleic acid 47 and the nucleic acid 47 sequence.

Different pore labels exhibiting different spectral absorption maxima may be attached to a single pore. The nucleic acid may be modified with corresponding acceptor dye labeled nucleotides where each donor label forms FRET pairs with one acceptor labeled nucleotide (i.e. multi-color FRET). Each of the four nucleotides may contain a specific acceptor label which gets excited by one or more of the pore donor labels. The base of the pore may be illuminated with different color light sources to accommodate the excitation of the different donor labels. Alternatively, e.g., where Quantum dots are used as donor labels, the broad absorption spectra characteristic of Quantum dots may allow for a single wavelength light source to sufficiently illuminate/excite the different donor labels which exhibit different spectral absorption maxima.

A single pore donor label (e.g., a single Quantum dot) may be suitable for exciting one nucleic acid acceptor label. For example, four different pore donor labels may be provided where each donor label can excite one of four different nucleic acid acceptor labels resulting in the emission of four distinct wavelengths. A single pore donor label (e.g., a single Quantum dot) may be suitable for exciting two or more nucleic acid acceptor labels that have similar absorption spectra overlapping with the donor label emission spectrum and show different emission spectra (i.e. different Stoke's shifts), where each acceptor label emits light at a different wavelength after excitation by the single donor label. Two different pore donor labels (e.g., two Quantum dots having different emission or absorption spectra) may be suitable for exciting four nucleic acid acceptor labels having different emission or excitation spectra, which each emit light at different wavelengths. One donor label or Quantum dot may be capable of exciting two of the nucleic acid acceptor labels resulting in their emission of light at different wavelengths, and the other Quantum dot may be capable of exciting the other two nucleic acid acceptor labels resulting in their emission of light at different wavelengths. The above arrangements provide clean and distinct wavelength emissions from each nucleic acid acceptor label for accurate detection.

A nanopore may include one or more monomers or attachment points, e.g., about 7 attachment points, one on each of the seven monomers making up a particular protein nanopore, such as alpha-hemolysin. One or more different donor labels, e.g., Quantum dots, may attach one to each of the attachment points, e.g., a nanopore may have up to seven different Quantum dots attached thereto. A single donor label or Quantum dot may be used to excite all four different nucleic acid acceptor labels resulting in a common wavelength emission suitable for detecting a molecule or detecting the presence of a molecule, e.g., in a biosensor application.

For accumulation of the raw signal data where a multicolor FRET interaction is utilized, the emission wavelength of the four different acceptor labels may be filtered and recorded as a function of time and emission wavelength, which results in a direct read-out of sequence information.

As mentioned supra, a nucleic acid sample may be divided into four parts to sequence the nucleic acid. The four nucleic acid or DNA samples may be used as a template to synthesize a labeled complementary nucleic acid polymer. Each of the four nucleic acid samples may be converted in a way such that one of the four nucleotide types (Guanine, Adenine, Cytosine or Thymine) are replaced with the nucleotide's labeled counterpart or otherwise labeled by attaching a label to a respective nucleotide. The same label may be used for each nucleotide or optionally, different labels may be used. The remaining nucleotides are the naturally occurring nucleic acid building blocks. Optionally, two, three or each nucleotide of a nucleic acid may be replaced with a nucleotide carrying a distinct acceptor label.

To perform the sequence read-out where a single nucleotide label is utilized with the target nucleic acid split into four samples, each having one nucleotide labeled with the same, or optionally, a different acceptor label, a specially designed algorithm may be utilized which (i) corrects, (ii) defines, and (iii) aligns the four partial sequences into one master sequence. Each partial sequence displays the relative position of one of the four nucleotides in the context of the whole genome sequence, thus, four sequencing reactions may be required to determine the position of each nucleotide. The algorithm may correct for missing bases due to inefficient labeling of the nucleic acid. One type of nucleotide in a DNA molecule can be completely substituted with the nucleotide's fluorescent counterpart. Various inefficiencies in labeling may result in less than 100% coverage from this substitution. Fluorescently labeled nucleotides usually come at a purity of around 99%, i.e., approximately 1% of the nucleotides do not carry a label. Consequently, even at a 100% incorporation of modified nucleotides, 1% of the nucleotides may be unlabeled and may not be detectable by nanopore transfer sequencing.

One solution to this problem is a redundant coverage of the nucleic acid to be sequenced. Each sequence may be read multiple times, e.g., at least 50 times per sequencing reaction (i.e. a 50 fold redundancy). Thus, the algorithm will compare the 50 sequences which will allow a statistically sound determination of each nucleotide call.

The algorithm may define the relative position of the sequenced nucleotides in the template nucleic acid. For example, the time of the current blockage during the translocation process may be used to determine the relative position of the detected nucleotides. The relative position and the time of the occurrence of two signals may be monitored and used to determine the position of the nucleotides relative to each other. Optionally, a combination of the above methods may be used to determine the position of the nucleotides in the sequence.

The nucleic acid or DNA to be analyzed may be separated into four samples. Each sample will be used to exchange one form of nucleotide (A, G, T, or C) with the nucleotide's fluorescent counterpart. Four separate nanopore sequencing reactions may reveal the relative positions of the four nucleotides in the DNA sample through optical detection. A computer algorithm will then align the four sub-sequences into one master sequence. The same acceptor label capable of emitting light at a specific wavelength or color may be utilized in all four samples. Optionally, different labels having different wavelength emissions may be utilized.

For example, FIG. 4A shows partial contigs from nucleic acid sequencing utilizing a singly labeled nucleic acid. Four separate nanopore sequencing reactions take place. Each of the four separate nanopore sequencing reactions, which are created by the same type of nucleotide acceptor label, generates a sub-sequence that displays the relative position of one of the four nucleotides. A redundant coverage of each sequence may ensure statistical sound base calls and read-outs. A computer algorithm may be utilized to deduce the four partial contig sequences which are the common denominators of the multiple covered sub-sequences (i.e. G-contig, A-contig, T-contig, and C-contig).

Figure 4B:
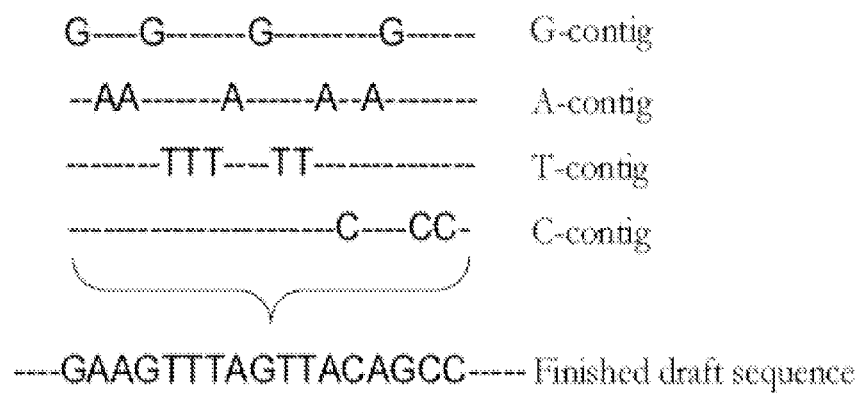
FIG. 4B illustrates how partial contig alignment may generate a first draft nucleic acid sequence.

FIG. 4B shows how partial contig alignment may generate a first draft nucleic acid sequence. For example, the second bioinformatic step involves alignment of the four contigs. Software searches for matching sequence stretches of the four contigs that complement each other. This step results in a finished draft sequence.

Optionally, both optical and electrical read-outs/detection may be utilized to sequence a nucleic acid. Electrical read-outs may be utilized to measure the number of non-labeled nucleotides in a sequence to help assess the relative position of a detected labeled nucleotide on a nucleic acid sequence. The length of the nucleic acid can be calculated by measuring the change in current through the nanopore and the duration of that current change. The methods and systems described herein may utilize solely optical read-outs or optical detection of energy emission or light emission by a labeled monomer to identify and sequence the monomer and to sequence a polymer including the monomer. Optionally, a combination of optical and electrical readouts or detection may be used.

A nucleotide acceptor label may be in the form of a quencher which may quench the transferred energy. In the case of a quenching nucleotide label, radiation emission from the pore donor label will decrease when a labeled nucleotide is in proximity to the donor label. The detection system for quenching pore labels is designed to maximize the radiation collected from the pore labels, while filtering out laser excitation radiation. For a quenching label, a decrease in photon counts of the pore label, such as a quantum dot, is interpreted as a labeled nucleotide.

Figure 5A:
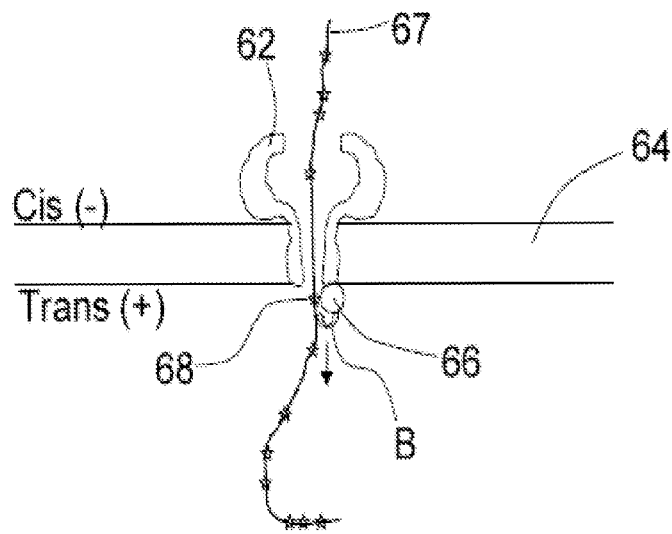
FIG. 5A illustrates one variation of a quenching interaction between a pore label on a protein nanopore and a nucleic acid label on a nucleic acid which is being translocated through the protein nanopore (the hydrophobic coating and lipid layer not being shown).

FIG. 5A shows one variation of a quenching interaction between a pore donor label 66 on a proteinaceous or protein pore or nanopore 62 and a nucleic acid quenching label 68 on a nucleic acid 67 (e.g., a single or double stranded nucleic acid), which is being translocated through the protein nanopore 62. The protein nanopore 62 is positioned in a lipid bilayer 64.

During a continuous illumination of the pore label 66 the pore label 66 emits light at a certain wavelength which is detected with an appropriate optical or other detection system. The quenching label 68 positioned on a nucleotide of nucleic acid 67 comes in close proximity to the pore label 66, e.g., as or after the label 68 or labeled nucleotide exits the nanopore 62, and thereby quenches the pore label 66 (which is indicated by arrow B). This quenching is detected by a decrease or sharp decrease in measured photons emitted from the nanopore label.

Figure 5B:
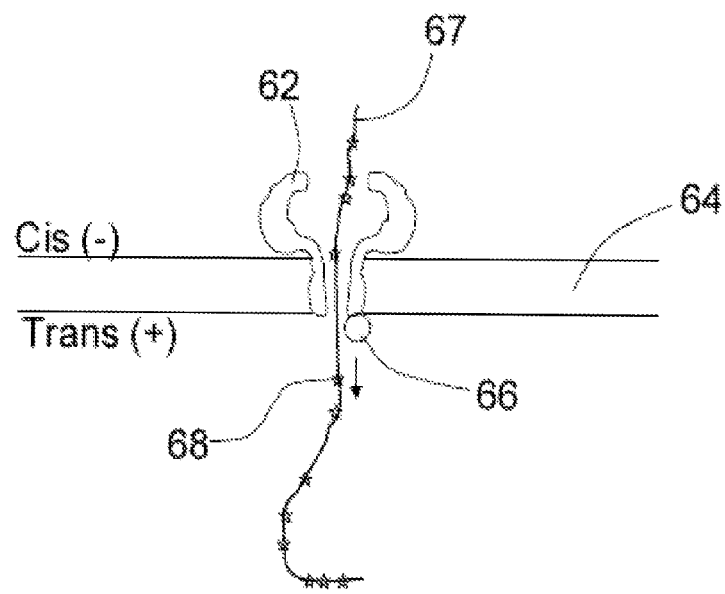
FIG. 5B illustrates translocation of a labeled nucleic acid through a protein nanopore at a point in time where no quenching is taking place (the hydrophobic coating and lipid layer not being shown).

FIG. 5B shows translocation of the labeled nucleic acid 67 at a point in time where no quenching is taking place (due to the labels not being in close enough proximity to each other). This is indicated by the lack of any arrows showing energy transfer between a pore label 66 and a nucleic acid label 68.

The energy transfer reaction, energy emission or pore label quenching as described above may take place as or before the label or labeled nucleotide enters the nanopore, e.g., on the cis side of the nanopore.

The labeling system may be designed to emit energy continuously without intermittency or rapid photobleaching of the fluorophores. For example, the buffer compartment of a pore holder may contain an oxygen depletion system that will remove dissolved Oxygen from the system via enzymatical, chemical or electrochemical means thereby reducing photobleaching of the fluorophore labeled nucleic acid.

An oxygen depletion system is a buffer solution containing components that selectively react with dissolved oxygen. Removing oxygen from the sequencing buffer solution helps prevent photobleaching of the fluorophore labels. An example of a composition of an oxygen depletion buffer is as follows: 10 mM tris-Cl, pH 8.0, 50 mM NaCl, 10 mM MgCl2, 1% (v/v) 2-mercaptoethanol, 4 mg/ml glucose, 0.1 mg/ml glucose oxidase, and 0.04 mg/ml catalase (Sabanayagam, C. R. et al., J. Chem. Phys. 123 (2005): 224708). The buffer is degassed by sonication before use to extend the buffer's useful lifetime by first removing oxygen mechanically. The buffer system then removes oxygen via the enzymatic oxidation of glucose by glucose oxidase.

The sequencing buffer may also contain components that prevent fluorescence intermittency, also referred to as "blinking," in one or both of the quantum dot labeled pores and fluorophore labeled nucleic acids. The phenomenon of blinking occurs when the excited fluorophore transitions to a non-radiative triplet state. Individual fluorophores may display fluorescence intermittency known as blinking in which the fluorophore transitions to and from the fluorophore's emitting and dark state. Blinking can interfere with certain aspects of the sequencing schemes. Blinking may be prevented or left alone. The triplet state is responsible for blinking in many organic fluorophores and that blinking can be suppressed with chemicals that quench the triplet state.

Molecules such as Trolox (6-hydroxy-2,5,7,8-tetramethylchroman-2-carboxylic acid) are effective in eliminating blinking for fluorophores or dyes such as Cy5 (Rasnik, I. et al., Nat Methods 11 (2006): 891-893). Certain Quantum dots may display blinking, however, CdTe quantum dots produced by aqueous synthesis in the presence of mercaptopropionic acid have recently been shown to emit continuously without blinking (He, H. et al., Angew. Chem. Int. Ed. 45 (2006): 7588-7591). CdTe quantum dots are ideally suited as labels to be utilized in the methods described herein, since they are water soluble with high quantum yield and can be directly conjugated through the terminal carboxylic acid groups of the mercaptopropionic acid ligands.

The labels may be made resistant to photobleaching and blinking With an efficient oxygen depletion system, Cy5 fluorophores can undergo ~$10^5$ cycles of excitation and emission before irreversible degradation. If the incident laser light is of high enough efficiency that excitation of the Cy5 fluorophore is saturated (re-excited immediately after emission) than the rate of photon emission is determined by the fluorescence lifetime of the Cy5 fluorophore. Since the Cy5 fluorophore has a lifetime on the order of 1 ns, and an assumed FRET efficiency of 10%, up to 10,000 photons can be emitted as the Cy5 labeled nucleotide transverses the nanopore. Microscopes used for single molecule detection are typically around 3% efficient in light collection. This can provide ~300 photons detected for a given label, which provides sufficiently high signal to noise ratio for single base detection.

A polymer or nucleic acid may be translocated through a nanopore having a suitable diameter (the diameter may vary, e.g., the diameter may be about 2 to 6 nm) at an approx. speed of 1,000 to 100,000 or 1,000 to 10,000 nucleotides per second. Each base of the nucleic acid may be fluorescently labeled with a distinct fluorophore. The base of the nanopore may be labeled with a quantum dot. When the nucleotide label comes in close proximity to the quantum dot, a non-radiative, quantum resonance energy transfer occurs which results in light emission of a specific wavelength form the nucleotide label.

The characteristic broad absorption peak of the quantum dot allows for a short excitation wavelength which doesn't interfere with the detection of the longer emission wavelength. The emission peak of the quantum dot has a significant spectral overlap with the absorption peak of the acceptor fluorophore. This overlap may result in an energy transfer from the quantum dot to the fluorophore which then emits photons of a specific wavelength. These fluorophore emitted photons are subsequently detected by an appropriate optical system. The efficiency of the energy transfer may be highly dependent on the distance between the donor and acceptor, with a 50% efficiency at the so called Foerster radius.

Sequencing may be performed by utilizing one or more pores or nanopores simultaneously. For example, a plurality of nanopores may be positioned in parallel or in any configuration in one or more lipid bilayers or substrates in order to expedite the sequencing process and sequence many nucleic acid molecules or other biological polymers at the same time.

A plurality of pores may be configured on a rotatable disc or substrate. When donor labels or quantum dots become substantially or completely used, burned out or exhausted (i.e., they reached their fluorescent lifetime), the disc or substrate may be rotated, thereby rotating a fresh pore with fresh donor labels or quantum dots into place to receive nucleic acids and continue sequencing. The electrical field which pulls the nucleic acid through the pore may be turned off during rotation of the disc and then turned back on once a new pore is in position for sequencing. Optionally, the electric field may be left on continuously.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

EXAMPLE

In this example, a silicon nitride solid phase membrane was treated at different helium ion beam energies and reductions in autofluorescence were measured. Next, nanopores were created in separate silicon nitride membranes, one having been treated by a method described herein to bleach autofluorescence and the other being untreated, after which fluorescently labeled DNA was driven through the respective nanopores. The treatment and fabrication of the nanopores were both carried out using a Orion Plus helium ion microscope (Carl Zeiss, Germany). The nanopores were fabricated as taught in Yang et al, Nanotechnology, 22: 285310 (2011) (available online at stacks.iop.org/Nano/22/285310). A lambda DNA (48.5 kb long) was prepared and driven through a nanopore as described in Yang et al (cited above), except that the lambda DNA had a single Cy3 label attached to one end. A 532 nm solid state laser was used to excite the Cy3 label at 13 mWatt. Emitted photons were collected by a 60× oil immersion objective of an IX71 inverted microscope (Olympus Inc.) and detected with a CMOS camera (Flash 4.0, Hamamatsu Corp.) at a frame rate of 500 Hz. Data analysis was performed with ImageJ and Igor. Results are shown in FIGS. 6 and 7, respectively.

Figure 6:
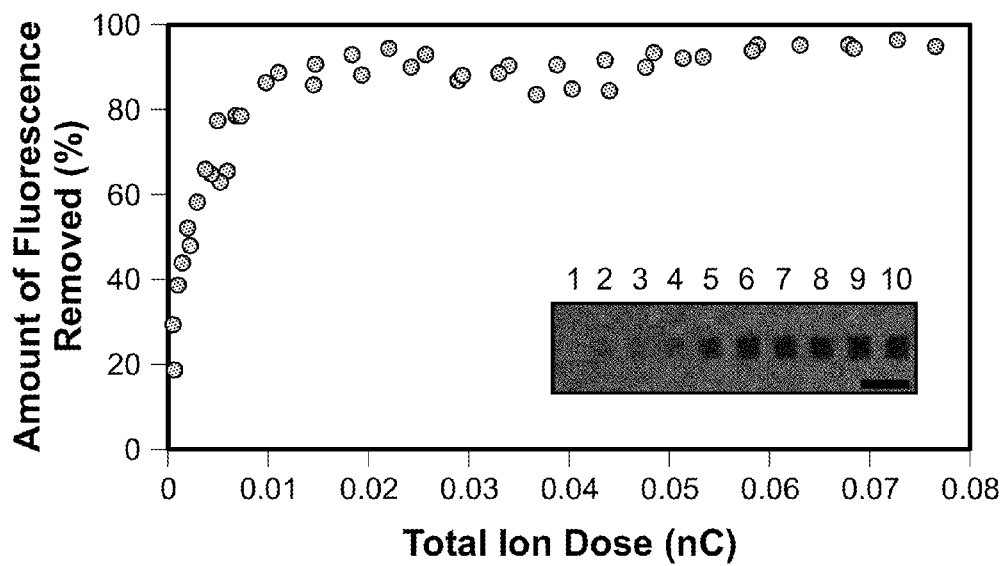
FIG. 6 illustrates results from one embodiment wherein a silicon nitride substrate is treated with a helium ion beam.

FIG. 6 show autofluorescence reduction data as a percentage of the fluorescence of an untreated silicon nitride membrane versus ion dose (in nanoCoulombs, nC). Over the range of treatment levels, from 0 to 0.08 nC, the percentage reduction rapidly rose to nearly 100 percent at the 0.02 nC dose, after which it leveled for the higher doses to 0.08 nC. The reduction in autofluorescence is also demonstrated visually in the inset, which shows ten 5 um×5 um patches that were treated with increasing doses of helium ion beam, from 0 nC at patch "1" rising to 0.09 nC at patch "10".

Figure 7:
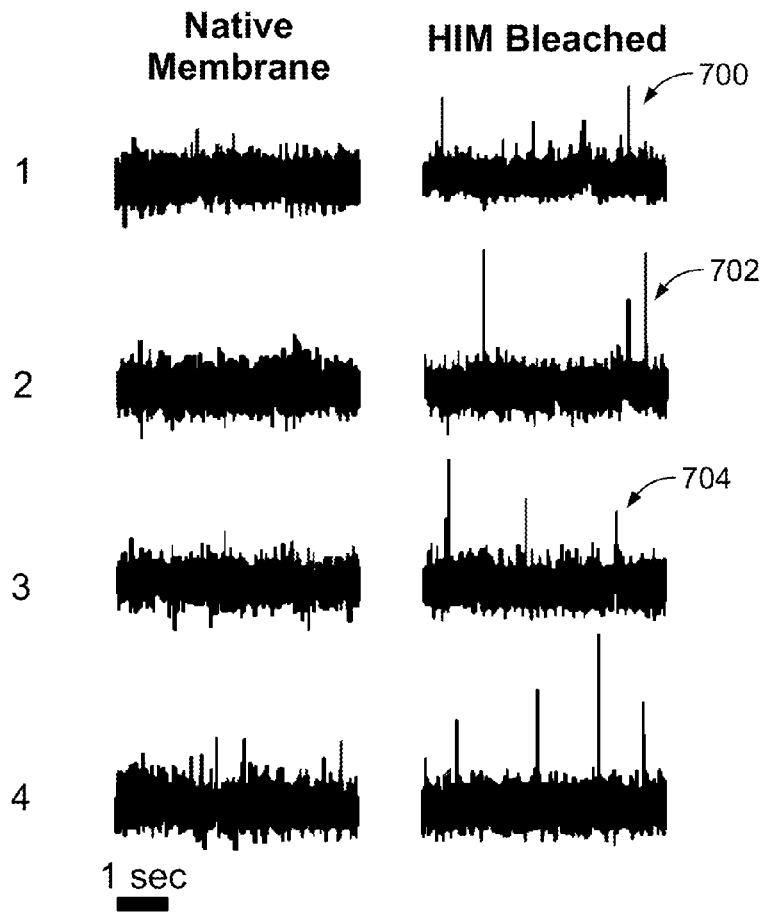
FIG. 7 shows optical signals from labeled DNA transported through a nanopore microfabricated in silicon nitride, without treatment (native membrane) and with treatment (HIM bleached) in accordance with the variations or methods described herein.

FIG. 7 shows plots of fluorescence versus time for four replicate pairs of experiments where Cy3-labeled linearized lambda phage DNA was translocated through nanopores in treated versus untreated silicon nitride membranes. The plots on the left are from untreated membranes and the plots on the right are from treated membranes. The experimental set-up was essentially the same as that described in Yang et al (cited above), except for the DNA here was fluorescently labeled and fluorescence instead of conductance was measured. In the data corresponding to the untreated membrane, the background fluorescence noise is so high that the signals from transiting DNA is completely obscured, whereas in the treated material signals corresponding to transiting DNA is clearly seen. The pronounced peaks (for example, 700, 702 and 704) correspond to the labeled DNA transiting the nanopore in the treated silicon nitride membrane.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

What is claimed is:

1. A method of reducing background fluorescence in a nanopore array comprising a membrane of optically active MEMS material, the method comprising the step of treating a surface of the optically active MEMS material with a low energy helium ion beam without melting, vaporization, deformation or sputtering in the membrane and with fluorescence background reduction that permits single fluorophores transiting nanopores of the nanopore array to be detected.

2. The method of claim 1, wherein said MEMS material is silicon nitride.

3. The method of claim 2, wherein said low energy helium ion beam delivers to said surface of said silicon nitride a dosage in the range of from 2e-10 to 8e-10 nC/nm^2.

4. The method of claim 1, wherein said step of treating includes directing to said surface a helium ion beam that delivers thereto a dose in the range of from 2e-10 to 8e-10 nC/nm^2.

5. The method of claim 1 wherein said detection is carried out with a microscope configured for single molecule detection.

6. The method of claim 1 wherein said MEMS material is selected from the group consisting of silicon nitride, silicon dioxide and aluminum oxide.

* * * * *